US012799181B2

(12) United States Patent
Huang

(10) Patent No.: US 12,799,181 B2
(45) Date of Patent: Nov. 17, 2026

(54) HIGH-AFFINITY T CELL RECEPTOR THAT RECOGNIZES SSX2

(71) Applicant: XLIFESC, LTD., Guangdong (CN)

(72) Inventor: Jinhua Huang, Guangzhou (CN)

(73) Assignee: XLIFESC, LTD., Guangdong (CN)

( * ) Notice: Subject to any disclaimer, the term of this patent is extended or adjusted under 35 U.S.C. 154(b) by 1251 days.

(21) Appl. No.: 17/640,601

(22) PCT Filed: Sep. 4, 2020

(86) PCT No.: PCT/CN2020/113583
§ 371 (c)(1),
(2) Date: Mar. 4, 2022

(87) PCT Pub. No.: WO2021/043284
PCT Pub. Date: Mar. 11, 2021

(65) Prior Publication Data

US 2022/0402997 A1 Dec. 22, 2022

(30) Foreign Application Priority Data

Sep. 5, 2019 (CN) ......................... 201910837691.3

(51) Int. Cl.

| | |
|---|---|
| ***C07K 14/705*** | (2006.01) |
| ***A61K 38/00*** | (2006.01) |
| ***A61K 40/11*** | (2025.01) |
| ***A61K 40/32*** | (2025.01) |
| ***A61K 40/42*** | (2025.01) |
| ***C07K 16/30*** | (2006.01) |
| ***C12N 5/0783*** | (2010.01) |
| ***C12N 15/85*** | (2006.01) |

(52) U.S. Cl.
CPC .......... *C07K 14/7051* (2013.01); *A61K 40/11* (2025.01); *A61K 40/32* (2025.01); *A61K 40/4267* (2025.01); *C07K 16/30* (2013.01); *C12N 5/0636* (2013.01); *C12N 15/85* (2013.01); *A61K 38/00* (2013.01); *C07K 2317/52* (2013.01); *C07K 2317/565* (2013.01); *C07K 2317/622* (2013.01)

(58) Field of Classification Search
CPC ........................... C07K 14/7051; C07K 16/30; C07K 2317/52; C07K 2317/565; C07K 2317/622; C07K 16/2809; C07K 2317/75; C07K 2319/33; C07K 2317/32; C07K 2317/92; C07K 2318/00; C07K 19/00; A61K 40/11; A61K 40/32; A61K 40/4267; A61K 38/00; C12N 5/0636; C12N 15/85; C12N 2510/00; A61P 35/00
See application file for complete search history.

(56) References Cited

U.S. PATENT DOCUMENTS

2007/0105779 A1 5/2007 Valmori et al.

FOREIGN PATENT DOCUMENTS

| | | | |
|---|---|---|---|
| CN | 103124740 | A | 5/2013 |
| CN | 103249430 | A | 8/2013 |
| CN | 105683215 | A | 6/2016 |
| CN | 106279404 | A | 1/2017 |
| CN | 108602874 | A | 9/2018 |
| CN | 110950949 | A | 4/2020 |
| EP | 3858852 | A1 | 8/2021 |
| EP | 4006050 | A1 | 6/2022 |
| EP | 4047014 | A1 | 8/2022 |
| NL | 2014935 | | 12/2016 |
| WO | 2019002444 | A1 | 1/2019 |
| WO | 2020194195 | A1 | 10/2020 |

OTHER PUBLICATIONS

Abate-Daga et al. 2014. PLOS ONE 9(3): e93321. PMID: 24681846. (Year: 2014).*
Briney et al. Nature. Feb. 2019; 566(7744):393-397. PMID: 30664748. (Year: 2019).*
Rasin et al. 2021. Mol Ther Methods Clin Dev. Oct. 1, 2021;23:296-306. PMID: 34729377. (Year: 2021).*
Mo et al. 2023. Expert Rev Mol Med. Dec. 14, 2023;26:e4. PMID: 38095091 (Year: 2023).*
Lin et al. 2025. Theranostics. Jan. 1, 2025; 15(1):300-323. PMID: 39744228. (Year: 2025).*
Abate-Daga et al., "Development of a T Cell Receptor Targeting an HLA-A0201 Restricted Epitope from the Cancer-Testis Antigen SSX2 for Adoptive Immunotherapy of Cancer," PLoS One, vol. 9, No. 3, Mar. 2014, e93321.
Hinrichs et al., "Exploiting the curative potential of adoptive T-cell therapy for cancer," Immunological Reviews, vol. 257, No. 1, Jan. 2015, pp. 56-71.
Linnemann et al., "High-throughput identification of antigen-specific TCRs by TCR gene capture," Nature Medicine, vol. 19, Oct. 2013, pp. 1534-1541.
International Search Report and Written Opinion issued on Dec. 10, 2020 in PCT Application No. PCT/CN2020/113583.
Notice of Grant of Invention Patent Right issued in CN Application No. 201910837691.3 on Jan. 5, 2023 and its English translation, 6 pages.
Extended European Search Report issued in EP Application No. 20859846.6 on May 25, 2023, 8 pages.

(Continued)

*Primary Examiner* — Thomas J. Visone
(74) *Attorney, Agent, or Firm* — ArentFox Schiff LLP; Daniel W. Clarke

(57) ABSTRACT

Provided is a high-affinity T cell receptor (TCR) that recognizes SSX2, wherein the TCR has the property of binding to a KASEKIFYV (SEQ ID NO: 29)-HLA A0201 complex, and the binding affinity of the TCR to the KASEKIFYV (SEQ ID NO: 29)-HLA A0201 complex is at least twice the binding affinity of a wild-type TCR to the KASEKIFYV (SEQ ID NO: 29)-HLA A0201 complex. Also provided is a fusion molecule of such a TCR with a therapeutic agent. Such a TCR can be used alone or in combination with a therapeutic agent to target tumor cells presenting the KASEKIFYV (SEQ ID NO: 29)-HLA A0201 complex.

12 Claims, 3 Drawing Sheets

Specification includes a Sequence Listing.

(56) References Cited

OTHER PUBLICATIONS

Abate-Daga et al., "Development of a T Cell Receptor Targeting an HLA-A*0201 Restricted Epitope from the Cancer-Testis Antigen SSX2 for Adoptive Immunotherapy of Cancer," PLOS ONE, vol. 9, Iss. 3, pp. 1-12, 2014.
Hou et al., "Synopsis of Humam SSX Gene Family," Journal of Sichuan Teachers College, vol. 23, No. 3, pp. 1-4, 2002.
Xie et al., "Expression and Application of SSX, NY-ESO-1, BRDT and MAGE-C2 Genes in Malignant Car-cinoma Including Gastric Tumor," Medical Recapitulate, Iss. 2, pp. 210-212, 2009.
First Office Action of Chinese Patent Application No. 201910837691.3 mailed on Apr. 21, 2022, along with English language translation thereof.

* cited by examiner

AQTVTQSQPEMSVQEAETVTLSCTYDTSESDYYLFWYKQPPSRQMILVIRQEAYKQQNATENRFSVNFQ
KAAKSFSLKISDSQLGDAAMYFCAYRSGIIQGAQKLVFGQGTRLTINP (SEQ ID NO:1)

Figure 1a

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSDRELLFYNEQFFGPGTRLTVL (SEQ ID NO:2)

Figure 1b

AQTVTQSQPELSVQEGETVTISCTYDTSESDYYLFWYKQPPSRQPILVIRQEAYKQQNATENRFSVNFQ
KAAKSFSLKISDVQPGDAAMYFCAYRSGIIQGAQKLVFGQGTRLTINP (SEQ ID NO:3)

Figure 2a

AAGVTQSPRHLSVEKGETVTLKCYPIPRHDTVYWYQQGPGQDLQFLISFYEKMQSDKGSIPDRFSAQQF
SDYHSELNISSVEPGDSALYFCASSSDRELLFYNEQFFGPGTRLTVD (SEQ ID NO:4)

Figure 2b

GCTCAAACTGTTACTCAGAGCCAACCGGAGCTGAGCGTGCAAGAGGGTGAAACCGTTACCATCAGCTGC
ACCTACGACACCAGCGAAAGCGATTACTACCTGTTCTGGTATAAGCAGCCGCCGAGCCGTCAACCGATC
CTGGTTATTCGTCAGGAAGCGTACAAACAGCAAAACGCGACCGAAAACCGTTTCAGCGTGAACTTTCAG
AAGGCGGCGAAAAGCTTCAGCCTGAAGATCAGCGACGTTCAACCGGGCGATGCGGCGATGTACTTTTGC
GCGTATCGTAGCGGTATCATTCAGGGCGCGCAAAAACTGGTGTTCGGTCAGGGCACCCGTCTGACCATT
AACCCG (SEQ ID NO:5)

Figure 3a

GCGGCGGGCGTGACCCAAAGCCCGCGTCACCTGAGCGTGGAGAAGGGTGAAACCGTTACCCTGAAATGC
TATCCGATCCCGCGTCACGACACCGTTTACTGGTATCAGCAAGGTCCGGGCCAGGATCTGCAATTCCTG
ATCAGCTTTTACGAGAAGATGCAGAGCGACAAAGGTAGCATTCCGGATCGTTTCAGCGCGCAGCAATTT
AGCGACTATCACAGCGAGCTGAACATTAGCAGCGTGGAACCGGGTGACAGCGCGCTGTACTTCTGCGCG
AGCAGCAGCGATCGTGAGCTGCTGTTTTATAACGAACAGTTCTTTGGTCCGGGCACCCGTCTGACCGTT
GAT (SEQ ID NO:6)

Figure 3b

GGGSEGGGSEGGGSEGGGSEGGTG (SEQ ID NO:7)

Figure 4a

GGTGGCGGTAGCGAGGGCGGTGGCAGCGAAGGTGGCGGTAGCGAGGGCGGTGGCAGCGAAGGTGGCACC
GGT (SEQ ID NO:8)

Figure 4b

AQTVTQSQPELSVQEGETVTISCTYDTSESDYYLFWYKQPPSRQPILVIRQEAYKQQNATENRFSVNFQ
KAAKSFSLKISDVQPGDAAMYFCAYRSGIIQGAQKLVFGQGTRLTINPGGGSEGGGSEGGGSEGGGSEG
GTGAAGVTQSPRHLSVEKGETVTLKCYPIPRHDTVYWYQQGPGQDLQFLISFYEKMQSDKGSIPDRFSA
QQFSDYHSELNISSVEPGDSALYFCASSSDRELLFYNEQFFGPGTRLTVD (SEQ ID NO:9)

Figure 5a

GCTCAaACtGTtACtCAGAGCCAACCGGAGCTGAGCGTGCAAGAGGGTGAAACCGTTACCATCAGCTGC
ACCTACGACACCAGCGAAAGCGATTACTACCTGTTCTGGTATAAGCAGCCGCCGAGCCGTCAACCGATC
CTGGTTATTCGTCAGGAAGCGTACAAACAGCAAAACGCGACCGAAAACCGTTTCAGCGTGAACTTTCAG
AAGGCGGCGAAAAGCTTCAGCCTGAAGATCAGCGACGTTCAACCGGGCGATGCGGCGATGTACTTTTGC
GCGTATCGTAGCGGTATCATTCAGGGCGCGCAAAAACTGGTGTTCGGTCAGGGCACCCGTCTGACCATT
AACCCGGGTGGCGGTAGCGAGGGCGGTGGCAGCGAAGGTGGCGGTAGCGAGGGCGGTGGCAGCGAAGGT
GGCACCGGTGCGGCGGGCGTGACCCAAAGCCCGCGTCACCTGAGCGTGGAGAAGGGTGAAACCGTTACC
CTGAAATGCTATCCGATCCCGCGTCACGACACCGTTTACTGGTATCAGCAAGGTCCGGGCCAGGATCTG
CAATTCCTGATCAGCTTTTACGAGAAGATGCAGAGCGACAAAGGTAGCATTCCGGATCGTTTCAGCGCG
CAGCAATTTAGCGACTATCACAGCGAGCTGAACATTAGCAGCGTGGAACCGGGTGACAGCGCGCTGTAC
TTCTGCGCGAGCAGCAGCGATCGTGAGCTGCTGTTTTATAACGAACAGTTCTTTGGTCCGGGCACCCGT
CTGACCGTTGAT (SEQ ID NO:10)

Figure 5b

AQTVTQSQPEMSVQEAETVTLSCTYDTSESDYYLFWYKQPPSRQMILVIRQEAYKQQNATENRFSVNFQ
KAAKSFSLKISDSQLGDAAMYFCAYRSGIIQGAQKLVFGQGTRLTINPNIQNPDPAVYQLRDSKSSDKS
VCLFTDFDSQTNVSQSKDSDVYITDKCVLDMRSMDFKSNSAVAWSNKSDFACANAFNNSIIPEDTFFPS
PESS (SEQ ID NO:11)

Figure 6a

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSDRELLFYNEQFFGPGTRLTVLEDLKNVFPPEVAVFEPSEAEIS
HTQKATLVCLATGFYPDHVELSWWVNGKEVHSGVCTDPQPLKEQPALNDSRYALSSRLRVSATFWQDPR
NHFRCQVQFYGLSENDEWTQDRAKPVTQIVSAEAWGRAD (SEQ ID NO:12)

Figure 6b

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSDRIPPYYNEQFFGPGTRLTVL (SEQ ID NO:13)

Figure 7(1)

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSVRELNYVDEQFFGPGTRLTVL (SEQ ID NO:14)

Figure 7(2)

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSDRELNDAPEQFFGPGTRLTVL (SEQ ID NO:15)

Figure 7(3)

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSDRELVFNPEQFFGPGTRLTVL (SEQ ID NO:16)

Figure 7(4)

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSDRELLDAPEQFFGPGTRLTVL (SEQ ID NO:17)

Figure 7(5)

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSDRELLFPDLTFFGPGTRLTVL (SEQ ID NO:18)

Figure 7(6)

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSDRELIHPEEQFFGPGTRLTVL (SEQ ID NO:19)

Figure 7(7)

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSDRELLFYAVPHFGPGTRLTVL (SEQ ID NO:20)

Figure 7(8)

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSDRELLNPEEQFFGPGTRLTVL (SEQ ID NO:21)

Figure 7(9)

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSDRELEHPEEQFFGPGTRLTVL (SEQ ID NO:22)

Figure 7(10)

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSDRELPFVPEQFFGPGTRLTVL (SEQ ID NO:23)

Figure 7(11)

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSDRELVFKPEQFFGPGTRLTVL (SEQ ID NO:24)

Figure 7(12)

AQTVTQSQPEMSVQEAETVTLSCTYDTSESDYYLFWYKQPPSRQMILVIRQEAYKQQNATENRFSVNFQ
KAAKSFSLKISDSQLGDAAMYFCAYRSGIIQGAQKLVFGQGTRLTINPNIQNPDPAVYQLRDSKSSDKS
VCLFTDFDSQTNVSQSKDSDVYITDKTVLDMRSMDFKSNSAVAWSNKSDFACANAFNNSIIPEDTFFPS
PESS (SEQ ID NO:25)

Figure 8a

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSDRELLFYNEQFFGPGTRLTVLEDLKNVFPPEVAVFEPSEAEIS
HTQKATLVCLATGFYPDHVELSWWVNGKEVHSGVSTDPQPLKEQPALNDSRYCLSSRLRVSATFWQNPR
NHFRCQVQFYGLSENDEWTQDRAKPVTQIVSAEAWGRAD (SEQ ID NO:26)

Figure 8b

AQTVTQSQPEMSVQEAETVTLSCTYDTSESDYYLFWYKQPPSRQMILVIRQEAYKQQNATENRFSVNFQ
KAAKSFSLKISDSQLGDAAMYFCAYRSGIIQGAQKLVFGQGTRLTINPNIQNPDPAVYQLRDSKSSDKS
VCLFTDFDSQTNVSQSKDSDVYITDKTVLDMRSMDFKSNSAVAWSNKSDFACANAFNNSIIPEDTFFPS
PESSCDVKLVEKSFETDTNLNFQNLSVIGFRILLLKVAGFNLLMTLRLWSS (SEQ ID NO:27)

Figure 9a

AAGVIQSPRHLIKEKRETATLKCYPIPRHDTVYWYQQGPGQDPQFLISFYEKMQSDKGSIPDRFSAQQF
SDYHSELNMSSLELGDSALYFCASSSDRELLFYNEQFFGPGTRLTVLEDLKNVFPPEVAVFEPSEAEIS
HTQKATLVCLATGFYPDHVELSWWVNGKEVHSGVSTDPQPLKEQPALNDSRYCLSSRLRVSATFWQNPR
NHFRCQVQFYGLSENDEWTQDRAKPVTQIVSAEAWGRADCGFTSESYQQGVLSATILYEILLGKATLYA
VLVSALVLMAMVKRKDSRG (SEQ ID NO:28)

Figure 9b

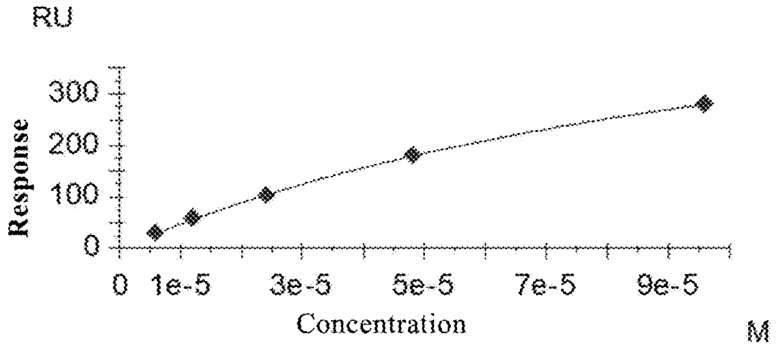

Figure 10

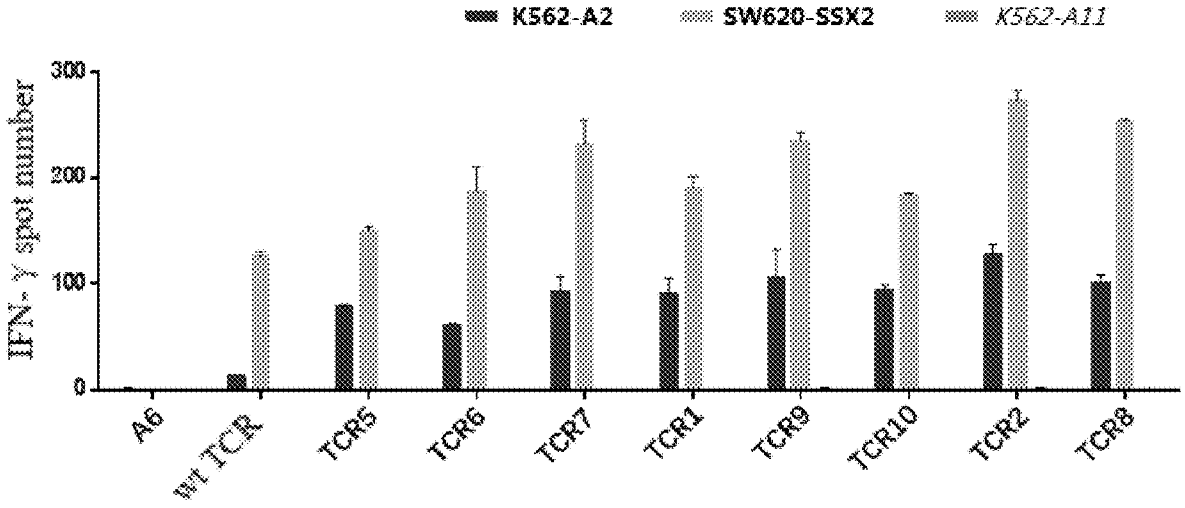

Figure 11

```
SEQUENCE LISTING

<160> NUMBER OF SEQ ID NOS: 48

<210> SEQ ID NO 1
<211> LENGTH: 117
<212> TYPE: PRT
<213> ORGANISM: Artificial sequence
<220> FEATURE:
<223> OTHER INFORMATION: polypeptide

<400> SEQUENCE: 1

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Gly Ile Ile Gln Gly Ala Gln Lys Leu Val Phe Gly Gln Gly Thr Arg
            100                 105                 110

Leu Thr Ile Asn Pro
        115


<210> SEQ ID NO 2
<211> LENGTH: 116
<212> TYPE: PRT
<213> ORGANISM: Artificial sequence
<220> FEATURE:
<223> OTHER INFORMATION: polypeptide

<400> SEQUENCE: 2

Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45
```

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Asp
                85                  90                  95

Arg Glu Leu Leu Phe Tyr Asn Glu Gln Phe Phe Gly Pro Gly Thr Arg
            100                 105                 110

Leu Thr Val Leu
        115

<210> SEQ ID NO 3
<211> LENGTH: 117
<212> TYPE: PRT
<213> ORGANISM: Artificial sequence
<220> FEATURE:
<223> OTHER INFORMATION: polypeptide

<400> SEQUENCE: 3

Ala Gln Thr Val Thr Gln Ser Gln Pro Glu Leu Ser Val Gln Glu Gly
1               5                   10                  15

Glu Thr Val Thr Ile Ser Cys Thr Tyr Asp Thr Ser Glu Ser Asp Tyr
            20                  25                  30

Tyr Leu Phe Trp Tyr Lys Gln Pro Pro Ser Arg Gln Pro Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Val Gln Pro Gly Asp Ala Ala Met Tyr Phe Cys Ala Tyr Arg Ser
                85                  90                  95

Gly Ile Ile Gln Gly Ala Gln Lys Leu Val Phe Gly Gln Gly Thr Arg
            100                 105                 110

Leu Thr Ile Asn Pro
        115

<210> SEQ ID NO 4
<211> LENGTH: 116
<212> TYPE: PRT
<213> ORGANISM: Artificial sequence
<220> FEATURE:
<223> OTHER INFORMATION: polypeptide

<400> SEQUENCE: 4

Ala Ala Gly Val Thr Gln Ser Pro Arg His Leu Ser Val Glu Lys Gly
1               5                   10                  15

Glu Thr Val Thr Leu Lys Cys Tyr Pro Ile Pro Arg His Asp Thr Val
            20                  25                  30

Tyr Trp Tyr Gln Gln Gly Pro Gly Gln Asp Leu Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Ile Ser Ser
65                  70                  75                  80

Val Glu Pro Gly Asp Ser Ala Leu Tyr Phe Cys Ala Ser Ser Ser Asp
                85                  90                  95

Arg Glu Leu Leu Phe Tyr Asn Glu Gln Phe Phe Gly Pro Gly Thr Arg 100 105 110

Leu Thr Val Asp
115

<210> SEQ ID NO 5
<211> LENGTH: 351
<212> TYPE: DNA
<213> ORGANISM: Artificial sequence
<220> FEATURE:
<223> OTHER INFORMATION: polynucleotide

<400> SEQUENCE: 5
gctcaaactg ttactcagag ccaaccggag ctgagcgtgc aagagggtga aaccgttacc 60
atcagctgca cctacgacac cagcgaaagc gattactacc tgttctggta taagcagccg 120
ccgagccgtc aaccgatcct ggttattcgt caggaagcgt acaaacagca aaacgcgacc 180
gaaaaccgtt tcagcgtgaa ctttcagaag gcggcgaaaa gcttcagcct gaagatcagc 240
gacgttcaac cgggcgatgc ggcgatgtac ttttgcgcgt atcgtagcgg tatcattcag 300
ggcgcgcaaa aactggtgtt cggtcagggc acccgtctga ccattaaccc g 351

<210> SEQ ID NO 6
<211> LENGTH: 348
<212> TYPE: DNA
<213> ORGANISM: Artificial sequence
<220> FEATURE:
<223> OTHER INFORMATION: polynucleotide

<400> SEQUENCE: 6
gcggcgggcg tgacccaaag cccgcgtcac ctgagcgtgg agaagggtga aaccgttacc 60
ctgaaatgct atccgatccc gcgtcacgac accgtttact ggtatcagca aggtccgggc 120
caggatctgc aattcctgat cagcttttac gagaagatgc agagcgacaa aggtagcatt 180
ccggatcgtt tcagcgcgca gcaatttagc gactatcaca gcgagctgaa cattagcagc 240
gtggaaccgg gtgacagcgc gctgtacttc tgcgcgagca gcagcgatcg tgagctgctg 300
ttttataacg aacagttctt tggtccgggc acccgtctga ccgttgat 348

<210> SEQ ID NO 7
<211> LENGTH: 24
<212> TYPE: PRT
<213> ORGANISM: Artificial sequence
<220> FEATURE:
<223> OTHER INFORMATION: a synthesized flexible short peptide

<400> SEQUENCE: 7

Gly Gly Gly Ser Glu Gly Gly Gly Ser Glu Gly Gly Gly Ser Glu Gly
1 5 10 15

Gly Gly Ser Glu Gly Gly Thr Gly
20

<210> SEQ ID NO 8
<211> LENGTH: 72
<212> TYPE: DNA
<213> ORGANISM: Artificial sequence
<220> FEATURE:
<223> OTHER INFORMATION: polynucleotide

<400> SEQUENCE: 8
ggtggcggta gcgagggcgg tggcagcgaa ggtggcggta gcgagggcgg tggcagcgaa 60
ggtggcaccg gt 72

<210> SEQ ID NO 9
<211> LENGTH: 257
<212> TYPE: PRT
<213> ORGANISM: Artificial sequence
<220> FEATURE:
<223> OTHER INFORMATION: polypeptide

<400> SEQUENCE: 9

```
Ala Gln Thr Val Thr Gln Ser Gln Pro Glu Leu Ser Val Gln Glu Gly
1               5                   10                  15

Glu Thr Val Thr Ile Ser Cys Thr Tyr Asp Thr Ser Glu Ser Asp Tyr
            20                  25                  30

Tyr Leu Phe Trp Tyr Lys Gln Pro Pro Ser Arg Gln Pro Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Val Gln Pro Gly Asp Ala Ala Met Tyr Phe Cys Ala Tyr Arg Ser
                85                  90                  95

Gly Ile Ile Gln Gly Ala Gln Lys Leu Val Phe Gly Gln Gly Thr Arg
            100                 105                 110

Leu Thr Ile Asn Pro Gly Gly Gly Ser Glu Gly Gly Gly Ser Glu Gly
        115                 120                 125

Gly Gly Ser Glu Gly Gly Gly Ser Glu Gly Gly Thr Gly Ala Ala Gly
    130                 135                 140

Val Thr Gln Ser Pro Arg His Leu Ser Val Glu Lys Gly Glu Thr Val
145                 150                 155                 160

Thr Leu Lys Cys Tyr Pro Ile Pro Arg His Asp Thr Val Tyr Trp Tyr
                165                 170                 175

Gln Gln Gly Pro Gly Gln Asp Leu Gln Phe Leu Ile Ser Phe Tyr Glu
            180                 185                 190

Lys Met Gln Ser Asp Lys Gly Ser Ile Pro Asp Arg Phe Ser Ala Gln
        195                 200                 205

Gln Phe Ser Asp Tyr His Ser Glu Leu Asn Ile Ser Ser Val Glu Pro
    210                 215                 220

Gly Asp Ser Ala Leu Tyr Phe Cys Ala Ser Ser Ser Asp Arg Glu Leu
225                 230                 235                 240

Leu Phe Tyr Asn Glu Gln Phe Phe Gly Pro Gly Thr Arg Leu Thr Val
                245                 250                 255

Asp
```

<210> SEQ ID NO 10
<211> LENGTH: 771
<212> TYPE: DNA
<213> ORGANISM: Artificial sequence
<220> FEATURE:
<223> OTHER INFORMATION: polynucleotide

<400> SEQUENCE: 10

```
gctcaaactg ttactcagag ccaaccggag ctgagcgtgc aagagggtga aaccgttacc     60

atcagctgca cctacgacac cagcgaaagc gattactacc tgttctggta taagcagccg    120

ccgagccgtc aaccgatcct ggttattcgt caggaagcgt acaaacagca aaacgcgacc    180

gaaaaccgtt tcagcgtgaa ctttcagaag gcggcgaaaa gcttcagcct gaagatcagc    240

gacgttcaac cgggcgatgc ggcgatgtac ttttgcgcgt atcgtagcgg tatcattcag    300
```

```
ggcgcgcaaa aactggtgtt cggtcagggc acccgtctga ccattaaccc gggtggcggt    360

agcgagggcg gtggcagcga aggtggcggt agcgagggcg gtggcagcga aggtggcacc    420

ggtgcggcgg gcgtgaccca aagcccgcgt cacctgagcg tggagaaggg tgaaaccgtt    480

accctgaaat gctatccgat cccgcgtcac gacaccgttt actggtatca gcaaggtccg    540

ggccaggatc tgcaattcct gatcagcttt tacgagaaga tgcagagcga caaaggtagc    600

attccggatc gtttcagcgc gcagcaattt agcgactatc acagcgagct gaacattagc    660

agcgtggaac cgggtgacag cgcgctgtac ttctgcgcga gcagcagcga tcgtgagctg    720

ctgttttata acgaacagtt ctttggtccg ggcacccgtc tgaccgttga t             771
```

<210> SEQ ID NO 11
<211> LENGTH: 211
<212> TYPE: PRT
<213> ORGANISM: Artificial sequence
<220> FEATURE:
<223> OTHER INFORMATION: polypeptide

<400> SEQUENCE: 11

```
Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Gly Ile Ile Gln Gly Ala Gln Lys Leu Val Phe Gly Gln Gly Thr Arg
            100                 105                 110

Leu Thr Ile Asn Pro Asn Ile Gln Asn Pro Asp Pro Ala Val Tyr Gln
        115                 120                 125

Leu Arg Asp Ser Lys Ser Ser Asp Lys Ser Val Cys Leu Phe Thr Asp
    130                 135                 140

Phe Asp Ser Gln Thr Asn Val Ser Gln Ser Lys Asp Ser Asp Val Tyr
145                 150                 155                 160

Ile Thr Asp Lys Cys Val Leu Asp Met Arg Ser Met Asp Phe Lys Ser
                165                 170                 175

Asn Ser Ala Val Ala Trp Ser Asn Lys Ser Asp Phe Ala Cys Ala Asn
            180                 185                 190

Ala Phe Asn Asn Ser Ile Ile Pro Glu Asp Thr Phe Phe Pro Ser Pro
        195                 200                 205

Glu Ser Ser
    210
```

<210> SEQ ID NO 12
<211> LENGTH: 246
<212> TYPE: PRT
<213> ORGANISM: Artificial sequence
<220> FEATURE:
<223> OTHER INFORMATION: polypeptide

<400> SEQUENCE: 12

```
Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Asp
                85                  90                  95

Arg Glu Leu Leu Phe Tyr Asn Glu Gln Phe Phe Gly Pro Gly Thr Arg
            100                 105                 110

Leu Thr Val Leu Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Cys Thr Asp Pro
                165                 170                 175

Gln Pro Leu Lys Glu Gln Pro Ala Leu Asn Asp Ser Arg Tyr Ala Leu
            180                 185                 190

Ser Ser Arg Leu Arg Val Ser Ala Thr Phe Trp Gln Asp Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp
                245


<210> SEQ ID NO 13
<211> LENGTH: 116
<212> TYPE: PRT
<213> ORGANISM: Artificial sequence
<220> FEATURE:
<223> OTHER INFORMATION: polypeptide

<400> SEQUENCE: 13

Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Asp
                85                  90                  95

Arg Ile Pro Pro Tyr Tyr Asn Glu Gln Phe Phe Gly Pro Gly Thr Arg
            100                 105                 110
```

```
Leu Thr Val Leu
        115


<210> SEQ ID NO 14
<211> LENGTH: 116
<212> TYPE: PRT
<213> ORGANISM: Artificial sequence
<220> FEATURE:
<223> OTHER INFORMATION: polypeptide

<400> SEQUENCE: 14

Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Val
                85                  90                  95

Arg Glu Leu Asn Tyr Val Asp Glu Gln Phe Phe Gly Pro Gly Thr Arg
            100                 105                 110

Leu Thr Val Leu
        115


<210> SEQ ID NO 15
<211> LENGTH: 116
<212> TYPE: PRT
<213> ORGANISM: Artificial sequence
<220> FEATURE:
<223> OTHER INFORMATION: polypeptide

<400> SEQUENCE: 15

Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Asp
                85                  90                  95

Arg Glu Leu Asn Asp Ala Pro Glu Gln Phe Phe Gly Pro Gly Thr Arg
            100                 105                 110

Leu Thr Val Leu
        115


<210> SEQ ID NO 16
<211> LENGTH: 116
<212> TYPE: PRT
<213> ORGANISM: Artificial sequence
<220> FEATURE:
<223> OTHER INFORMATION: polypeptide
```

<400> SEQUENCE: 16

```
Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Asp
                85                  90                  95

Arg Glu Leu Val Phe Asn Pro Glu Gln Phe Phe Gly Pro Gly Thr Arg
            100                 105                 110

Leu Thr Val Leu
        115
```

<210> SEQ ID NO 17
<211> LENGTH: 116
<212> TYPE: PRT
<213> ORGANISM: Artificial sequence
<220> FEATURE:
<223> OTHER INFORMATION: polypeptide

<400> SEQUENCE: 17

```
Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Asp
                85                  90                  95

Arg Glu Leu Leu Asp Ala Pro Glu Gln Phe Phe Gly Pro Gly Thr Arg
            100                 105                 110

Leu Thr Val Leu
        115
```

<210> SEQ ID NO 18
<211> LENGTH: 116
<212> TYPE: PRT
<213> ORGANISM: Artificial sequence
<220> FEATURE:
<223> OTHER INFORMATION: polypeptide

<400> SEQUENCE: 18

```
Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45
```

```
Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Asp
                85                  90                  95

Arg Glu Leu Leu Phe Pro Asp Leu Thr Phe Phe Gly Pro Gly Thr Arg
            100                 105                 110

Leu Thr Val Leu
        115


<210> SEQ ID NO 19
<211> LENGTH: 116
<212> TYPE: PRT
<213> ORGANISM: Artificial sequence
<220> FEATURE:
<223> OTHER INFORMATION: polypeptide

<400> SEQUENCE: 19

Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Asp
                85                  90                  95

Arg Glu Leu Ile His Pro Glu Glu Gln Phe Phe Gly Pro Gly Thr Arg
            100                 105                 110

Leu Thr Val Leu
        115


<210> SEQ ID NO 20
<211> LENGTH: 116
<212> TYPE: PRT
<213> ORGANISM: Artificial sequence
<220> FEATURE:
<223> OTHER INFORMATION: polypeptide

<400> SEQUENCE: 20

Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Asp
                85                  90                  95

Arg Glu Leu Leu Phe Tyr Ala Val Pro His Phe Gly Pro Gly Thr Arg
            100                 105                 110
```

```
Leu Thr Val Leu
        115


<210> SEQ ID NO 21
<211> LENGTH: 116
<212> TYPE: PRT
<213> ORGANISM: Artificial sequence
<220> FEATURE:
<223> OTHER INFORMATION: polypeptide

<400> SEQUENCE: 21

Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Asp
                85                  90                  95

Arg Glu Leu Leu Asn Pro Glu Glu Gln Phe Phe Gly Pro Gly Thr Arg
            100                 105                 110

Leu Thr Val Leu
        115


<210> SEQ ID NO 22
<211> LENGTH: 116
<212> TYPE: PRT
<213> ORGANISM: Artificial sequence
<220> FEATURE:
<223> OTHER INFORMATION: polypeptide

<400> SEQUENCE: 22

Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Asp
                85                  90                  95

Arg Glu Leu Glu His Pro Glu Glu Gln Phe Phe Gly Pro Gly Thr Arg
            100                 105                 110

Leu Thr Val Leu
        115


<210> SEQ ID NO 23
<211> LENGTH: 116
<212> TYPE: PRT
<213> ORGANISM: Artificial sequence
<220> FEATURE:
<223> OTHER INFORMATION: polypeptide
```

<400> SEQUENCE: 23

Ala Ala Gly Val Ile Gln Ser Pro Arg His Leu Ile Lys Glu Lys Arg
1 5 10 15

Glu Thr Ala Thr Leu Lys Cys Tyr Pro Ile Pro Arg His Asp Thr Val
20 25 30

Tyr Trp Tyr Gln Gln Gly Pro Gly Gln Asp Pro Gln Phe Leu Ile Ser
35 40 45

Phe Tyr Glu Lys Met Gln Ser Asp Lys Gly Ser Ile Pro Asp Arg Phe
50 55 60

Ser Ala Gln Gln Phe Ser Asp Tyr His Ser Glu Leu Asn Met Ser Ser
65 70 75 80

Leu Glu Leu Gly Asp Ser Ala Leu Tyr Phe Cys Ala Ser Ser Ser Asp
85 90 95

Arg Glu Leu Pro Phe Val Pro Glu Gln Phe Phe Gly Pro Gly Thr Arg
100 105 110

Leu Thr Val Leu
115

<210> SEQ ID NO 24
<211> LENGTH: 116
<212> TYPE: PRT
<213> ORGANISM: Artificial sequence
<220> FEATURE:
<223> OTHER INFORMATION: polypeptide

<400> SEQUENCE: 24

Ala Ala Gly Val Ile Gln Ser Pro Arg His Leu Ile Lys Glu Lys Arg
1 5 10 15

Glu Thr Ala Thr Leu Lys Cys Tyr Pro Ile Pro Arg His Asp Thr Val
20 25 30

Tyr Trp Tyr Gln Gln Gly Pro Gly Gln Asp Pro Gln Phe Leu Ile Ser
35 40 45

Phe Tyr Glu Lys Met Gln Ser Asp Lys Gly Ser Ile Pro Asp Arg Phe
50 55 60

Ser Ala Gln Gln Phe Ser Asp Tyr His Ser Glu Leu Asn Met Ser Ser
65 70 75 80

Leu Glu Leu Gly Asp Ser Ala Leu Tyr Phe Cys Ala Ser Ser Ser Asp
85 90 95

Arg Glu Leu Val Phe Lys Pro Glu Gln Phe Phe Gly Pro Gly Thr Arg
100 105 110

Leu Thr Val Leu
115

<210> SEQ ID NO 25
<211> LENGTH: 211
<212> TYPE: PRT
<213> ORGANISM: Artificial sequence
<220> FEATURE:
<223> OTHER INFORMATION: polypeptide

<400> SEQUENCE: 25

Ala Gln Thr Val Thr Gln Ser Gln Pro Glu Met Ser Val Gln Glu Ala
1 5 10 15

Glu Thr Val Thr Leu Ser Cys Thr Tyr Asp Thr Ser Glu Ser Asp Tyr
20 25 30

Tyr Leu Phe Trp Tyr Lys Gln Pro Pro Ser Arg Gln Met Ile Leu Val
35 40 45

```
Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Gly Ile Ile Gln Gly Ala Gln Lys Leu Val Phe Gly Gln Gly Thr Arg
            100                 105                 110

Leu Thr Ile Asn Pro Asn Ile Gln Asn Pro Asp Pro Ala Val Tyr Gln
        115                 120                 125

Leu Arg Asp Ser Lys Ser Ser Asp Lys Ser Val Cys Leu Phe Thr Asp
    130                 135                 140

Phe Asp Ser Gln Thr Asn Val Ser Gln Ser Lys Asp Ser Asp Val Tyr
145                 150                 155                 160

Ile Thr Asp Lys Thr Val Leu Asp Met Arg Ser Met Asp Phe Lys Ser
                165                 170                 175

Asn Ser Ala Val Ala Trp Ser Asn Lys Ser Asp Phe Ala Cys Ala Asn
            180                 185                 190

Ala Phe Asn Asn Ser Ile Ile Pro Glu Asp Thr Phe Phe Pro Ser Pro
        195                 200                 205

Glu Ser Ser
    210


<210> SEQ ID NO 26
<211> LENGTH: 246
<212> TYPE: PRT
<213> ORGANISM: Artificial sequence
<220> FEATURE:
<223> OTHER INFORMATION: polypeptide

<400> SEQUENCE: 26

Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Asp
                85                  90                  95

Arg Glu Leu Leu Phe Tyr Asn Glu Gln Phe Phe Gly Pro Gly Thr Arg
            100                 105                 110

Leu Thr Val Leu Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Cys Leu
            180                 185                 190
```

```
Ser Ser Arg Leu Arg Val Ser Ala Thr Phe Trp Gln Asn Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp
                245


<210> SEQ ID NO 27
<211> LENGTH: 258
<212> TYPE: PRT
<213> ORGANISM: Artificial sequence
<220> FEATURE:
<223> OTHER INFORMATION: polypeptide

<400> SEQUENCE: 27

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Gly Ile Ile Gln Gly Ala Gln Lys Leu Val Phe Gly Gln Gly Thr Arg
            100                 105                 110

Leu Thr Ile Asn Pro Asn Ile Gln Asn Pro Asp Pro Ala Val Tyr Gln
        115                 120                 125

Leu Arg Asp Ser Lys Ser Ser Asp Lys Ser Val Cys Leu Phe Thr Asp
    130                 135                 140

Phe Asp Ser Gln Thr Asn Val Ser Gln Ser Lys Asp Ser Asp Val Tyr
145                 150                 155                 160

Ile Thr Asp Lys Thr Val Leu Asp Met Arg Ser Met Asp Phe Lys Ser
                165                 170                 175

Asn Ser Ala Val Ala Trp Ser Asn Lys Ser Asp Phe Ala Cys Ala Asn
            180                 185                 190

Ala Phe Asn Asn Ser Ile Ile Pro Glu Asp Thr Phe Phe Pro Ser Pro
        195                 200                 205

Glu Ser Ser Cys Asp Val Lys Leu Val Glu Lys Ser Phe Glu Thr Asp
    210                 215                 220

Thr Asn Leu Asn Phe Gln Asn Leu Ser Val Ile Gly Phe Arg Ile Leu
225                 230                 235                 240

Leu Leu Lys Val Ala Gly Phe Asn Leu Leu Met Thr Leu Arg Leu Trp
                245                 250                 255

Ser Ser


<210> SEQ ID NO 28
<211> LENGTH: 295
<212> TYPE: PRT
<213> ORGANISM: Artificial sequence
<220> FEATURE:
```

<223> OTHER INFORMATION: polypeptide

<400> SEQUENCE: 28

```
Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Asp
                85                  90                  95

Arg Glu Leu Leu Phe Tyr Asn Glu Gln Phe Phe Gly Pro Gly Thr Arg
            100                 105                 110

Leu Thr Val Leu Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Cys Leu
            180                 185                 190

Ser Ser Arg Leu Arg Val Ser Ala Thr Phe Trp Gln Asn Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp Cys Gly Phe Thr Ser Glu Ser Tyr Gln Gln
                245                 250                 255

Gly Val Leu Ser Ala Thr Ile Leu Tyr Glu Ile Leu Leu Gly Lys Ala
            260                 265                 270

Thr Leu Tyr Ala Val Leu Val Ser Ala Leu Val Leu Met Ala Met Val
        275                 280                 285

Lys Arg Lys Asp Ser Arg Gly
    290                 295
```

<210> SEQ ID NO 29
<211> LENGTH: 9
<212> TYPE: PRT
<213> ORGANISM: Artificial sequence
<220> FEATURE:
<223> OTHER INFORMATION: polypeptide

<400> SEQUENCE: 29

```
Lys Ala Ser Glu Lys Ile Phe Tyr Val
1               5
```

<210> SEQ ID NO 30
<211> LENGTH: 14
<212> TYPE: PRT
<213> ORGANISM: Artificial sequence
<220> FEATURE:
<223> OTHER INFORMATION: polypeptide

<400> SEQUENCE: 30

Ala Tyr Arg Ser Gly Ile Ile Gln Gly Ala Gln Lys Leu Val
1 5 10

<210> SEQ ID NO 31
<211> LENGTH: 7
<212> TYPE: PRT
<213> ORGANISM: Artificial sequence
<220> FEATURE:
<223> OTHER INFORMATION: polypeptide

<400> SEQUENCE: 31

Thr Ser Glu Ser Asp Tyr Tyr
1 5

<210> SEQ ID NO 32
<211> LENGTH: 8
<212> TYPE: PRT
<213> ORGANISM: Artificial sequence
<220> FEATURE:
<223> OTHER INFORMATION: polypeptide

<400> SEQUENCE: 32

Gln Glu Ala Tyr Lys Gln Gln Asn
1 5

<210> SEQ ID NO 33
<211> LENGTH: 5
<212> TYPE: PRT
<213> ORGANISM: Artificial sequence
<220> FEATURE:
<223> OTHER INFORMATION: polypeptide

<400> SEQUENCE: 33

Pro Arg His Asp Thr
1 5

<210> SEQ ID NO 34
<211> LENGTH: 6
<212> TYPE: PRT
<213> ORGANISM: Artificial sequence
<220> FEATURE:
<223> OTHER INFORMATION: polypeptide

<400> SEQUENCE: 34

Phe Tyr Glu Lys Met Gln
1 5

<210> SEQ ID NO 35
<211> LENGTH: 15
<212> TYPE: PRT
<213> ORGANISM: Artificial sequence
<220> FEATURE:
<223> OTHER INFORMATION: polypeptide

<400> SEQUENCE: 35

Ala Ser Ser Ser Asp Arg Ile Pro Pro Tyr Tyr Asn Glu Gln Phe
1 5 10 15

<210> SEQ ID NO 36
<211> LENGTH: 15
<212> TYPE: PRT
<213> ORGANISM: Artificial sequence
<220> FEATURE:

<223> OTHER INFORMATION:
polypeptide

<400> SEQUENCE: 36

Ala Ser Ser Ser Asp Arg Glu Leu Asn Asp Ala Pro Glu Gln Phe
1 5 10 15

<210> SEQ ID NO 37
<211> LENGTH: 15
<212> TYPE: PRT
<213> ORGANISM: Artificial sequence
<220> FEATURE:
<223> OTHER INFORMATION: polypeptide

<400> SEQUENCE: 37

Ala Ser Ser Ser Val Arg Glu Leu Asn Tyr Val Asp Glu Gln Phe
1 5 10 15

<210> SEQ ID NO 38
<211> LENGTH: 15
<212> TYPE: PRT
<213> ORGANISM: Artificial sequence
<220> FEATURE:
<223> OTHER INFORMATION: polypeptide

<400> SEQUENCE: 38

Ala Ser Ser Ser Asp Arg Glu Leu Leu Phe Tyr Asn Glu Gln Phe
1 5 10 15

<210> SEQ ID NO 39
<211> LENGTH: 15
<212> TYPE: PRT
<213> ORGANISM: Artificial sequence
<220> FEATURE:
<223> OTHER INFORMATION: polypeptide

<400> SEQUENCE: 39

Ala Ser Ser Ser Asp Arg Glu Leu Val Phe Asn Pro Glu Gln Phe
1 5 10 15

<210> SEQ ID NO 40
<211> LENGTH: 15
<212> TYPE: PRT
<213> ORGANISM: Artificial sequence
<220> FEATURE:
<223> OTHER INFORMATION: polypeptide

<400> SEQUENCE: 40

Ala Ser Ser Ser Asp Arg Glu Leu Leu Asp Ala Pro Glu Gln Phe
1 5 10 15

<210> SEQ ID NO 41
<211> LENGTH: 15
<212> TYPE: PRT
<213> ORGANISM: Artificial sequence
<220> FEATURE:
<223> OTHER INFORMATION: polypeptide

<400> SEQUENCE: 41

Ala Ser Ser Ser Asp Arg Glu Leu Leu Phe Pro Asp Leu Thr Phe
1 5 10 15

<210> SEQ ID NO 42
<211> LENGTH: 15
<212> TYPE: PRT
<213> ORGANISM: Artificial sequence
<220> FEATURE:

<223> OTHER INFORMATION: polypeptide

<400> SEQUENCE: 42

Ala Ser Ser Ser Asp Arg Glu Leu Ile His Pro Glu Glu Gln Phe
1 5 10 15

<210> SEQ ID NO 43
<211> LENGTH: 15
<212> TYPE: PRT
<213> ORGANISM: Artificial sequence
<220> FEATURE:
<223> OTHER INFORMATION: polypeptide

<400> SEQUENCE: 43

Ala Ser Ser Ser Asp Arg Glu Leu Leu Phe Tyr Ala Val Pro His
1 5 10 15

<210> SEQ ID NO 44
<211> LENGTH: 15
<212> TYPE: PRT
<213> ORGANISM: Artificial sequence
<220> FEATURE:
<223> OTHER INFORMATION: polypeptide

<400> SEQUENCE: 44

Ala Ser Ser Ser Asp Arg Glu Leu Leu Asn Pro Glu Glu Gln Phe
1 5 10 15

<210> SEQ ID NO 45
<211> LENGTH: 15
<212> TYPE: PRT
<213> ORGANISM: Artificial sequence
<220> FEATURE:
<223> OTHER INFORMATION: polypeptide

<400> SEQUENCE: 45

Ala Ser Ser Ser Asp Arg Glu Leu Glu His Pro Glu Glu Gln Phe
1 5 10 15

<210> SEQ ID NO 46
<211> LENGTH: 15
<212> TYPE: PRT
<213> ORGANISM: Artificial sequence
<220> FEATURE:
<223> OTHER INFORMATION: polypeptide

<400> SEQUENCE: 46

Ala Ser Ser Ser Asp Arg Glu Leu Pro Phe Val Pro Glu Gln Phe
1 5 10 15

<210> SEQ ID NO 47
<211> LENGTH: 15
<212> TYPE: PRT
<213> ORGANISM: Artificial sequence
<220> FEATURE:
<223> OTHER INFORMATION: polypeptide

<400> SEQUENCE: 47

Ala Ser Ser Ser Asp Arg Glu Leu Val Phe Lys Pro Glu Gln Phe
1 5 10 15

<210> SEQ ID NO 48
<211> LENGTH: 5
<212> TYPE: PRT
<213> ORGANISM: Artificial sequence
<220> FEATURE:
<223> OTHER INFORMATION: polypeptide -continued

```
<400> SEQUENCE: 48

Gly Gly Gly Gly Ser
1               5
```

HIGH-AFFINITY T CELL RECEPTOR THAT RECOGNIZES SSX2

RELATED APPLICATIONS

This application is a National Stage application, filed under 35 U.S.C. § 371, of International Application No. PCT/CN2020/113583, filed Sep. 4, 2020, which claims the benefit of priority under 35 U.S.C. § 119 to CN Application No. 201910837691.3, filed on Sep. 5, 2019, each of which is incorporated herein by reference in its entirety.

SEQUENCE LISTING

This application contains a Sequence Listing which has been submitted electronically in ASCII format and is hereby incorporated by reference in its entirety. Said ASCII copy, created on Aug. 24, 2022 is named 51766-504N01US_ST25_Sequence.txt and is 40 KB in size.

TECHNICAL FIELD

The present disclosure relates to the field of biotechnology, and in particular, to a T cell receptor (TCR) capable of recognizing a polypeptide derived from SSX2 protein. The present disclosure further relates to the preparation and uses of such receptors.

BACKGROUND

There are only two types of molecules that can recognize antigens in a specific manner. One is immunoglobulin or antibody and the other is T-cell receptor (TCR), which is α/β or γ/δ heterodimeric glycoprotein on cell membrane. The physical repertoire of TCR of an immune system is generated in thymus through V(D)J recombination, followed by positive and negative selections. In the peripheral environment, TCRs mediate the recognition of specific major histocompatibility complex-peptide complexes (pMHC) by T cells and, as such, are essential to the immunological functioning of cells in the immune system.

TCR is the only receptor for presenting specific peptide antigens in a major histocompatibility complex (MHC). The exogenous or endogenous peptides may be the only sign of abnormality in a cell. In the immune system, once antigen-specific TCRs bind with pMHC complexes, it causes direct physical contact of a T cell and an antigen-presenting cell (APC). Then, the interaction of other membrane molecules in the T cell and APC occurs and the subsequent cell signaling and other physiological responses are initiated so that a range of different antigen-specific T cells exert immune effects on their target cells.

Molecular ligands of MHC class I and class II corresponding to TCRs are also proteins of the immunoglobulin superfamily but are specific for antigen presentation, and different individuals have different MHCs, thereby presenting different short peptides in one protein antigen to the surface of respective APC cells. Human MHC is commonly referred to as HLA gene or HLA complex.

SSX2 is the synovial sarcoma, X (SSX) breakpoint, also known as HOM-MEL-40. SSX2 is one of ten highly homologous nucleic acid proteins in SSX family. SSX protein is a cancer-testis antigen, which is only expressed in tumor cells and testicular embryonic cells that do not express MHC. SSX2 is expressed in a variety of human cancer cells, including, but not limited to, liver cancer, lung cancer, fibrosarcoma, breast cancer, colon cancer, and prostate cancer. SSX2 is degraded into small molecule polypeptides after being produced in cells, and combined with MHC (major histocompatibility complex) molecules to form a complex, which is presented to the cell surface. KASEKIFYV (SEQ ID NO: 29) is a short peptide derived from SSX2 antigen and a target for treating SSX2-related diseases.

Therefore, KASEKIFYV (SEQ ID NO: 29)-HLA A0201 complex provides a marker for TCR targeting tumor cells. The TCR capable of binding to KASEKIFYV (SEQ ID NO: 29)-HLA A0201 complex has high application value for treating tumors. For example, a TCR capable of targeting the tumor cell marker can be used to deliver a cytotoxic agent or immunostimulatory agent to target cells, or have the same transformed into T cells, such that the T cell expressing the TCR can destroy the tumor cells and can be administered to a patient during the course of treatment of so called adoptive immunotherapy. For the former purpose, the ideal TCR has higher affinity, allowing the TCR to reside on the targeted cells for a long period of time. For the latter purpose, it is preferred to use a TCR with medium affinity. Accordingly, those skilled in the art are directed to developing TCRs that can be used to target tumor cell markers for different purposes.

SUMMARY

An object of the present disclosure is to provide a TCR having a higher affinity for KASEKIFYV (SEQ ID NO: 29)-HLA A0201 complex.

Another object of the present disclosure is to provide a method for preparing the TCR of the above type and use of the TCR of the above type.

In a first aspect of the present disclosure, a T cell receptor (TCR) is provided, which has an activity of binding to KASEKIFYV (SEQ ID NO: 29)-HLA A0201 complex.

In another preferred embodiment, an α chain variable domain of the TCR comprises an amino acid sequence having at least 90%, preferably at least 92%, more preferably at least 94% (e.g., may be at least 90%, 91%, 92%, 93%, 94%, 95%, 96%, 97%, 98%, 99% of sequence homology) of sequence homology with the amino acid sequence as shown in SEQ ID NO: 1; and/or a β chain variable domain of the TCR comprises an amino acid sequence having at least 90%, preferably at least 92%, more preferably at least 94% (e.g., may be at least 91%, 92%, 93%, 94%, 95%, 96%, 97%, 98%, 99% of sequence homology) of sequence homology with the amino acid sequence as shown in SEQ ID NO: 2.

In another preferred embodiment, the TCR contains a mutation in the β chain variable domain as shown in SEQ ID NO: 2, and the mutation is selected from one or more of D96V, E98I, L99P, L100E/I/N/P/V, F101D/H/N/Y, Y102A/K/N/P/V, N103A/D/E/P, E104L/V, Q105P/T and F106H, wherein amino acid residues are numbered as shown in SEQ ID NO: 2.

In another preferred embodiment, the TCRα chain variable domain comprises three CDR regions, wherein the amino acid sequence of CDR3α is AYRSGIIQGAQKLV (SEQ ID NO: 30).

In another preferred embodiment, the TCRα chain variable domain comprises three CDR regions, and the sequences of the three CDR regions are listed as follows:

CDR1α: TSESDYY; (SEQ ID NO: 31)

CDR2α: QEAYKQQN; (SEQ ID NO: 32)

CDR3α: AYRSGIIQGAQKLV. (SEQ ID NO: 30)

In another preferred embodiment, the amino acid sequence of the TCRα chain variable domain is SEQ ID NO: 1.

In another preferred embodiment, the TCRβ chain variable domain comprises three CDR regions, wherein the amino acid sequence of CDR1β is PRHDT (SEQ ID NO: 33); and the amino acid sequence of CDR2β is FYEKMQ (SEQ ID NO: 34).

In another preferred embodiment, CDR3β of the TCRβ chain variable domain is selected from the group consisting of ASSSDRIPPYYNEQF (SEQ ID NO: 35), ASSSDRELNDAPEQF (SEQ ID NO: 36), ASSSVRELNYVDEQF (SEQ ID NO: 37) and ASSSDRELLFYNEQF (SEQ ID NO: 38).

In another preferred embodiment, the TCR has CDRs selected from the group consisting of:

| CDR No. | CDR1α | CDR2α | CDR3α | CDRβ | CDR2β | CDR3β |
|---|---|---|---|---|---|---|
| 1 | TSESDYY (SEQ ID NO: 31) | QEAYKQQN (SEQ ID NO: 32) | AYRSGIIQGAQKLV (SEQ ID NO: 30) | PRHDT (SEQ ID NO: 33) | FYEKMQ (SEQ ID NO: 34) | ASSSDRIPPYYNEQF (SEQ ID NO: 35) |
| 2 | TSESDYY (SEQ ID NO: 31) | QEAYKQQN (SEQ ID NO: 32) | AYRSGIIQGAQKLV (SEQ ID NO: 30) | PRHDT (SEQ ID NO: 33) | FYEKMQ (SEQ ID NO: 34) | ASSSVRELNYVDEQF (SEQ ID NO: 37) |
| 3 | TSESDYY (SEQ ID NO: 31) | QEAYKQQN (SEQ ID NO: 32) | AYRSGIIQGAQKLV (SEQ ID NO: 30) | PRHDT (SEQ ID NO: 33) | FYEKMQ (SEQ ID NO: 34) | ASSSDRELNDAPEQF (SEQ ID NO: 36) |
| 4 | TSESDYY (SEQ ID NO: 31) | QEAYKQQN (SEQ ID NO: 32) | AYRSGIIQGAQKLV (SEQ ID NO: 30) | PRHDT (SEQ ID NO: 33) | FYEKMQ (SEQ ID NO: 34) | ASSSDRELVFNPEQF (SEQ ID NO: 39) |
| 5 | TSESDYY (SEQ ID NO: 31) | QEAYKQQN (SEQ ID NO: 32) | AYRSGIIQGAQKLV (SEQ ID NO: 30) | PRHDT (SEQ ID NO: 33) | FYEKMQ (SEQ ID NO: 34) | ASSSDRELLDAPEQF (SEQ ID NO: 40) |
| 6 | TSESDYY (SEQ ID NO: 31) | QEAYKQQN (SEQ ID NO: 32) | AYRSGIIQGAQKLV (SEQ ID NO: 30) | PRHDT (SEQ ID NO: 33) | FYEKMQ (SEQ ID NO: 34) | ASSSDRELLFPDLTF (SEQ ID NO: 41) |
| 7 | TSESDYY (SEQ ID NO: 31) | QEAYKQQN (SEQ ID NO: 32) | AYRSGIIQGAQKLV (SEQ ID NO: 30) | PRHDT (SEQ ID NO: 33) | FYEKMQ (SEQ ID NO: 34) | ASSSDRELIHPEEQF (SEQ ID NO: 42) |
| 8 | TSESDYY (SEQ ID NO: 31) | QEAYKQQN (SEQ ID NO: 32) | AYRSGIIQGAQKLV (SEQ ID NO: 30) | PRHDT (SEQ ID NO: 33) | FYEKMQ (SEQ ID NO: 34) | ASSSDRELLFYAVPH (SEQ ID NO: 43) |
| 9 | TSESDYY (SEQ ID NO: 31) | QEAYKQQN (SEQ ID NO: 32) | AYRSGIIQGAQKLV (SEQ ID NO: 30) | PRHDT (SEQ ID NO: 33) | FYEKMQ (SEQ ID NO: 34) | ASSSDRELLNPEEQF (SEQ ID NO: 44) |
| 10 | TSESDYY (SEQ ID NO: 31) | QEAYKQQN (SEQ ID NO: 32) | AYRSGIIQGAQKLV (SEQ ID NO: 30) | PRHDT (SEQ ID NO: 33) | FYEKMQ (SEQ ID NO: 34) | ASSSDRELEHPEEQF (SEQ ID NO: 45) |
| 11 | TSESDYY (SEQ ID NO: 31) | QEAYKQQN (SEQ ID NO: 32) | AYRSGIIQGAQKLV (SEQ ID NO: 30) | PRHDT (SEQ ID NO: 33) | FYEKMQ (SEQ ID NO: 34) | ASSSDRELPFVPEQF (SEQ ID NO: 46) |
| 12 | TSESDYY (SEQ ID NO: 31) | QEAYKQQN (SEQ ID NO: 32) | AYRSGIIQGAQKLV (SEQ ID NO: 30) | PRHDT (SEQ ID NO: 33) | FYEKMQ (SEQ ID NO: 34) | ASSSDRELVFKPEQF (SEQ ID NO: 47) |

In another preferred embodiment, the amino acid sequence of the α chain variable domain of the TCR is selected from: SEQ ID NO: 1; and/or the amino acid sequence of the β chain variable domain of the TCR is selected from: SEQ ID NOs: 13-24.

In another preferred embodiment, the TCR is selected from the group consisting of:

| TCR No. | Sequence of α chain variable domain SEQ ID NO: | Sequence of β chain variable domain SEQ ID NO: |
|---|---|---|
| 1 | 1 | 13 |
| 2 | 1 | 14 |
| 3 | 1 | 15 |
| 4 | 1 | 16 |
| 5 | 1 | 17 |
| 6 | 1 | 18 |
| 7 | 1 | 19 |
| 8 | 1 | 20 |
| 9 | 1 | 21 |

-continued

| TCR No. | Sequence of α chain variable domain SEQ ID NO: | Sequence of β chain variable domain SEQ ID NO: |
|---|---|---|
| 10 | 1 | 22 |
| 11 | 1 | 23 |
| 12 | 1 | 24 |

In another preferred embodiment, the affinity of the TCR for KASEKIFYV (SEQ ID NO: 29)-HLA A0201 complex is at least twice that of a wild-type TCR.

In another preferred embodiment of the present disclosure, the affinity of the TCR for KASEKIFYV (SEQ ID NO: 29)-HLA A0201 complex is at least twice, preferably at least five times, more preferably at least ten times that of a wild-type TCR.

In another preferred embodiment, the affinity of the TCR for KASEKIFYV (SEQ ID NO: 29)-HLA A0201 complex is at least 50 times, preferably at least 100 times, more preferably at least 300 times that of a wild-type TCR.

In particular, the dissociation equilibrium constant $K_D$ of the TCR to KASEKIFYV (SEQ ID NO: 29)-HLA A0201 complex is ≤50 μM.

In another preferred embodiment, the dissociation equilibrium constant of the TCR to KASEKIFYV (SEQ ID NO: 29)-HLA A0201 complex is 1 μM≤$K_D$≤50 μM.

In another preferred embodiment, the TCR is soluble.

In another preferred embodiment, the TCR is an αβ heterodimeric TCR. Preferably, the TCR has an α chain constant region sequence TRAC*01 and a β chain constant region sequence TRBC1*01 or TRBC2*01.

In another preferred embodiment, the TCR comprises (i) all or part of a TCR α chain other than its transmembrane domain, and (ii) all or part of a TCR β chain other than its transmembrane domain, wherein both of (i) and (ii) comprise a variable domain and at least a part of the constant domain of the TCR chain.

In another preferred embodiment, an artificial interchain disulfide bond is contained between an α chain constant region and a β chain constant region of the TCR.

In another preferred embodiment, cysteine residues forming the artificial interchain disulfide bond are substituted for one or more groups of amino acids selected from the following:

Thr48 of TRAC*01 exon 1 and Ser57 of TRBC1*01 or TRBC2*01 exon 1;

Thr45 of TRAC*01 exon 1 and Ser77 of TRBC1*01 or TRBC2*01 exon 1;

Tyr10 of TRAC*01 exon 1 and Ser17 of TRBC1*01 or TRBC2*01 exon 1;

Thr45 of TRAC*01 exon 1 and Asp59 of TRBC1*01 or TRBC2*01 exon 1;

Ser15 of TRAC*01 exon 1 and Glu15 of TRBC1*01 or TRBC2*01 exon 1;

Arg53 of TRAC*01 exon 1 and Ser54 of TRBC1*01 or TRBC2*01 exon 1;

Pro89 of TRAC*01 exon 1 and Ala19 of TRBC1*01 or TRBC2*01 exon 1; and

Tyr10 of TRAC*01 exon 1 and Glu20 of TRBC1*01 or TRBC2*01 exon 1.

In another preferred embodiment, the TCR is a single-chain TCR.

In another preferred embodiment, the TCR is a single-chain TCR consisting of an α chain variable domain and a β chain variable domain, and the α chain variable domain and the β chain variable domain are linked via a flexible short peptide sequence (linker).

In another preferred embodiment, a conjugate binds to an α chain and/or a β chain of the TCR at C- or N-terminal.

In another preferred embodiment, the conjugate that binds to the TCR is a detectable label, a therapeutic agent, a PK modified moiety or a combination thereof.

In another preferred embodiment, the therapeutic agent that binds to the TCR is an anti-CD3 antibody linked to the α or β chain of the TCR at C- or N-terminal.

In a second aspect of the present disclosure, a multivalent TCR complex comprising at least two TCR molecules is provided, wherein at least one of the TCR molecules is the TCR of the first aspect of the present disclosure.

In a third aspect of the present disclosure, a nucleic acid molecule is provided, which comprises a nucleic acid sequence encoding the TCR molecule of the first aspect of the present disclosure or the multivalent TCR complex of the second aspect of the present disclosure, or a complementary sequence thereof.

In a fourth aspect of the present disclosure, a vector is provided, which comprises the nucleic acid molecule of the third aspect of the present disclosure.

In a fifth aspect of the present disclosure, a host cell is provided, which comprises the vector of the fourth aspect of the present disclosure or has the exogenous nucleic acid molecule of the third aspect of the present disclosure integrated into a chromosome of the host cell.

In a sixth aspect of the present disclosure, an isolated cell is provided, which expresses the TCR of the first aspect of the present disclosure.

In a seventh aspect of the present disclosure, a pharmaceutical composition is provided, which comprises a pharmaceutically acceptable carrier, and the TCR of the first aspect of the present disclosure, or the TCR complex of the second aspect of the present disclosure, or the cell of the sixth aspect of the present disclosure.

In an eighth aspect of the present disclosure, a method for treating a disease is provided, which comprises administering an appropriate amount of the TCR of the first aspect of the present disclosure, or the TCR complex of the second aspect of the present disclosure, or the cell of the sixth aspect of the present disclosure, or the pharmaceutical composition of the seventh aspect of the present disclosure to a subject in need thereof.

In a ninth aspect of the present disclosure, use of the TCR of the first aspect of the present disclosure, or the TCR complex of the second aspect of the present disclosure, or the cell of the sixth aspect of the present disclosure is provided for preparing a medicament for treating a tumor, and preferably, the tumor is a SSX2-positive tumor.

In a tenth aspect of the present disclosure, the T cell receptor (TCR) of the first aspect of the present disclosure, or the TCR complex of the second aspect of the present disclosure, or the cell of the sixth aspect of the present disclosure is used as a medicament for treating a tumor. Preferably, the tumor is a SSX2-positive tumor.

In an eleventh aspect of the present disclosure, a method for preparing the T cell receptor of the first aspect of the present disclosure is provided, which comprises the steps of:

(i) culturing the host cell of the fifth aspect of the present disclosure to express the T cell receptor of the first aspect of the present disclosure; and (ii) isolating or purifying the T cell receptor.

It is to be understood that within the scope of the present disclosure, the preceding technical features of the present disclosure and the technical features specifically described hereinafter (as in the embodiments) may be combined with each other to constitute a new or preferred technical solution, which will not be repeated herein one by one.

BRIEF DESCRIPTION OF DRAWINGS

FIGS. 1*a* and 1*b* show the amino acid sequences of α and β chain variable domains of the wild-type TCR capable of specifically binding to KASEKIFYV (SEQ ID NO: 29)-HLA A0201 complex, respectively.

FIGS. 2*a* and 2*b* show the amino acid sequences of the α variable domain and the β chain variable domain of the single-chain template TCR constructed in the present disclosure, respectively.

FIGS. 3*a* and 3*b* show the DNA sequences of the α variable domain and the β chain variable domain of the single-chain template TCR constructed in the present disclosure, respectively.

FIGS. 4*a* and 4*b* are the amino acid sequence and nucleotide sequence of a linking short peptide (linker) of the single-chain template TCR constructed in the present disclosure, respectively.

FIGS. 5*a* and 5*b* the amino acid sequence and DNA sequence of the single-chain template TCR constructed in the present disclosure, respectively.

FIGS. 8*a* and 8*b* show the amino acid sequences of the soluble reference TCR α and β chains in the present disclosure, respectively.

FIGS. 7(1)-(12) show the amino acid sequences of the α chain variable domain of a heterodimeric TCR with high affinity for KASEKIFYV (SEQ ID NO: 29)-HLA A0201 complex, respectively, wherein the mutated residues are underlined.

FIGS. 8*a* and 8*b* show the extracellular amino acid sequences of α and β chains of the wild-type TCR capable of specifically binding to KASEKIFYV (SEQ ID NO: 29)-HLA A0201 complex, respectively.

FIGS. 9*a* and 8*b* show the amino acid sequences of α and β chains of the wild-type TCR capable of specifically binding to KASEKIFYV (SEQ ID NO: 29)-HLA A0201 complex, respectively.

FIG. 10 is a binding curve of a soluble reference TCR (i.e., the wild-type TCR) with KASEKIFYV (SEQ ID NO: 29)-HLA A0201 complex.

FIG. 11 shows results of activation experiment of effector cells transfected with the high-affinity TCR of the present disclosure.

DETAILED DESCRIPTION

Through extensive and intensive research, the present disclosure obtained a high-affinity T cell receptor (TCR) recognizing KASEKIFYV (SEQ ID NO: 29) short peptide (derived from AFP protein) which is presented in a form of KASEKIFYV (SEQ ID NO: 29)-HLA A0201 complex. The high-affinity TCR has a mutation in three CDR regions of its α chain variable domain:

```
                                    (SEQ ID NO: 31)
CDR1α: TSESDYY;
                                    (SEQ ID NO: 32)
CDR2α: QEAYKQQN;
```

CDR3α: AYRSGIIQGAQKLV (SEQ ID NO: 30); and/or has a mutation in three CDR regions of its β chain variable domain:

```
                                    (SEQ ID NO: 33)
CDR1β: PRHDT;
                                    (SEQ ID NO: 34)
CDR2β: FYEKMQ;
```

CDR3β: ASSSDRELLFYNEQF (SEQ ID NO: 38); and after mutation, the affinity and/or binding half-life of the TCR of the present disclosure for the above KASEKIFYV (SEQ ID NO: 29)-HLA A0201 complex is at least 2-fold greater than that of the wild-type TCR.

Before the present disclosure is described, it is to be understood that the present disclosure is not limited to the specific methods and experimental conditions described, as such methods and conditions may vary. It is also understood that the terminology used herein is for the purpose of describing particular embodiments and is not intended to be limiting, and the scope of the present disclosure shall be only limited by the appended claims.

All technical and scientific terms used herein have the same meaning as commonly understood by a skilled person in the art to which the present disclosure belongs, unless otherwise defined.

Although any methods and materials similar or equivalent to those described in the present disclosure can be used in the practice or testing of the present disclosure, the preferred methods and materials are exemplified herein.

Term

T-Cell Receptor (TCR)

The TCR may be described using the International ImMunoGeneTics Information System (IMGT). A native αβ heterodimeric TCR has an α chain and a β chain. Generally speaking, each chain comprises a variable region, a junction region and a constant region, and typically the β chain also contains a short hypervariable region between the variable region and the junction region. However, the hypervariable region is often considered as part of the junction region. The junction region of the TCR is determined by the unique TRAJ and TRBJ of the IMGT, and the constant region of the TCR is determined by TRAC and TRBC of the IMGT.

Each variable region comprises three complementarity-determining regions (CDRs), CDR1, CDR2 and CDR3, which are chimeric in the framework sequence. In IMGT nomenclature, different numbers of TRAV and TRBV refer to different Vα types and VP types, respectively. In the IMGT system, there are the following symbols for an α chain constant domain: TRAC*01, where "TR" represents a TCR gene, "A" represents an α chain gene, C represents the constant region, and "*01" represents allele gene 1. There are the following symbols for a β chain constant domain: TRBC1*01 or TRBC2*01, where "TR" represents a TCR gene, "B" represents a β chain gene, C represents the constant region, and "*01" represents allele gene 1. The constant region of the α chain is uniquely defined, and in the form of the β chain, there are two possible constant region genes "C1" and "C2". Those skilled in the art can obtain constant region gene sequences of TCR α and β chains through the disclosed IMGT database.

The α and β chains of the TCR are generally considered as having two "domains" respectively, that is, a variable domain and a constant domain. The variable domain consists of a variable region and a junction region linked to each other. Therefore, in the description and claims of the present application, a "TCR α chain variable domain" refers to TRAV and TRAJ regions linked together. Likewise, a "TCR β chain variable domain" refers to TRBV and TRBD/TRBJ regions linked together. Three CDRs of the TCR α chain variable domain are CDR1α, CDR2α and CDR3α, respectively; and three CDRs of the TCR β chain variable domain are CDR1β, CDR2β and CDR3β, respectively. The framework sequences of TCR variable domains of the present disclosure may be of murine or human origin, preferably of human origin. The constant domain of the TCR comprises an intracellular portion, a transmembrane region and an extracellular portion. To obtain a soluble TCR so as to determine the affinity of the TCR for KASEKIFYV (SEQ ID NO: 29)-HLA A0201 complex, the TCR of the present disclosure preferably does not comprise a transmembrane region. More preferably, the amino acid sequence of the TCR of the present disclosure refers to an extracellular amino acid sequence of the TCR.

TCR sequences used in the present disclosure are of human origin. The amino acid sequence of the α chain and the amino acid sequence of the β chain of the "wild type TCR" in the present disclosure are SEQ ID NO: 27 and SEQ ID NO: 28, respectively, as shown in FIGS. 9*a* and 9*b*. The amino acid sequences of the α chain and the β chain of a "reference TCR" in the present disclosure are SEQ ID NO: 11 and SEQ ID NO: 12, respectively, as shown in FIGS. 6*a* and 6*b*. The extracellular amino acid sequences of the α chain and the β chain of the "wild type TCR" in the present disclosure are SEQ ID NO: 25 and SEQ ID NO: 26, respectively, as shown in FIGS. 8*a* and 8*b*. In the present disclosure, the amino acid sequences of α and β chain variable domains of the wild type TCR capable of binding to KASEKIFYV (SEQ ID NO: 29)-HLA A0201 complex are SEQ ID NO: 1 and SEQ ID NO: 2, respectively, as shown in FIGS. 1*a* and 1*b*. In the present disclosure, the terms "polypeptide of the present disclosure", "TCR of the present disclosure" and "T-cell receptor of the present disclosure" are used interchangeably.

Natural Interchain Disulfide Bond and Artificial Interchain Disulfide Bond

A group of disulfide bonds is present between Cα and Cβ chains in the membrane proximal region of a native TCR, which is referred to as "natural interchain disulfide bonds" in the present disclosure. In the present disclosure, an interchain covalent disulfide bond which is artificially introduced and located at a position different from the position of the natural interchain disulfide bond is referred to as "artificial interchain disulfide bond".

For convenience of description, in the present disclosure, the positions of the amino acid sequences of TRAC*01 and TRBC1*01 or TRBC2*01 are sequentially numbered from N-terminal to C-terminal. For example, the 60th amino acid in the order from N-terminal to C-terminal in TRBC1*01 or TRBC2*01 is P (proline), which may be described as Pro60 of TRBC1*01 or TRBC2*01 exon 1 in the present disclosure and may also be expressed as the amino acid at position 60 of TRBC1*01 or TRBC2*01 exon 1. In another example, the 61st amino acid in the order from N-terminal to C-terminal in TRBC1*01 or TRBC2*01 is Q (glutamine), which may be described as Gln61 of TRBC1*01 or TRBC2*01 exon 1 in the present disclosure and may also be expressed as the amino acid at position 61 of TRBC1*01 or TRBC2*01 exon 1, and so on. In the present disclosure, the positions of the amino acid sequences of variable regions TRAV and TRBV are numbered according to the positions listed in the IMGT. For example, the position of an amino acid in TRAV is numbered as 46 in the IMGT, the amino acid is described in the present disclosure as the amino acid at position 46 of TRAV, and so on. In the present disclosure, if the positions of other amino acid sequences are specifically described, the special description shall prevail.

Tumor

The term "tumor" refers to the inclusion of all types of cancer cell growth or carcinogenic processes, metastatic tissues or malignant transformed cells, tissues or organs, regardless of pathological type or stage of infection. Examples of tumors include, without limitation, solid tumors, soft tissue tumors and metastatic lesions. Examples of solid tumors include malignant tumors of different organ systems, such as sarcoma, lung squamous cell carcinoma and cancer. For example, infected prostate, lung, breast, lymph, gastrointestinal (e.g., colon) and genitourinary tract (e.g., kidney, epithelial cells) and pharynx. Lung squamous cell carcinoma includes malignant tumors, for example, most of colon cancer, rectal cancer, renal cell carcinoma, liver cancer, non-small cell lung cancer, small intestine cancer and esophageal cancer. Metastatic lesions of the above cancer may likewise be treated and prevented using the methods and compositions of the present disclosure.

Detailed Description of the Present Disclosure

As is known to all, an α chain variable domain and a β chain variable domain of a TCR each contain three CDRs, which are similar to the complementarity-determining regions of an antibody. CDR3 interacts with an antigen short peptide, and CDR1 and CDR2 interact with HLA. Therefore, the CDRs of a TCR molecule determine their interaction with an antigen short peptide-HLA complex. The amino acid sequences of the α chain variable domain and the chain variable domain of a wild type TCR capable of binding a complex of antigen short peptide KASEKIFYV (SEQ ID NO: 29) and HLA A0201 (that is, KASEKIFYV (SEQ ID NO: 29)-HLA A0201 complex) are SEQ ID NO: 1 and SEQ ID NO: 2, respectively, which are discovered for the first time by the inventors. The wild type TCR has the following CDRs:

```
α chain variable domain CDR
                              (SEQ ID NO: 31)
CDR1α: TSESDYY

                              (SEQ ID NO: 32)
CDR2α: QEAYKQQN

                              (SEQ ID NO: 30)
CDR3α: AYRSGIIQGAQKLV

β chain variable domain CDR
                              (SEQ ID NO: 33)
CDR1β: PRHDT

                              (SEQ ID NO: 34)
CDR2β: FYEKMQ

                              (SEQ ID NO: 38)
CDR3β: ASSSDRELLFYNEQF.
```

In the present disclosure, a high-affinity TCR is obtained by subjecting mutation and screen in the above CDR regions, where the affinity of the high-affinity TCR for KASEKIFYV (SEQ ID NO: 29)-HLA A0201 complex is at least twice that of the wild-type TCR for KASEKIFYV (SEQ ID NO: 29)-HLA A0201 complex.

The present disclosure provides a T cell receptor (TCR) which has an activity of binding to KASEKIFYV (SEQ ID NO: 29)-HLA A0201 complex.

In the present disclosure, the three CDRs of the α chain variable domain (SEQ ID NO: 1) of the wild-type TCR, i.e., CDR1, CDR2 and CDR3, are located at positions 27-33, positions 51-58 and positions 93-106 of SEQ ID NO: 1, respectively.

In the present disclosure, the three CDRs of the β chain variable domain (SEQ ID NO: 2) of the wild-type TCR, i.e., CDR1, CDR2 and CDR3, are located at positions 27-31, positions 49-54 and positions 92-106 of SEQ ID NO: 2, respectively. Accordingly, amino acid residues are numbered as shown in SEQ ID NO: 2, 96D is D at position 5 of CDR3β, 98E is E at position 7 of CDR3β, 99L is L at position 8 of CDR3β, 100L is L at position 9 of CDR3β, 101F is F at position 10 of CDR11β, 102Y is Yat position 11 of CDR3β, 103N is N at position 12 of CDR3β, 104E is E at position 13 of CDR3β, 105Q is Q at position 14 of CDR3β, and 106F is F at position 15 of CDR3β.

Preferably, the mutated TCR β chain variable domain comprises one or more amino acid residues selected from the group consisting of: 96V; 98I; 99P; 100E, 100I, 100N, 100P or 100V; 101D, 101H, 101N or 101Y; 102A, 102K, 102N, 102P or 102V; 103A, 103D, 103E or 103P; 104L or 104V; 105P or 105T; and 106H; wherein the amino acid residue is numbered as shown in SEQ ID NO: 2.

More specifically, in the β chain variable domain, specific forms of the mutation comprise one or more of D96V, E98I, L99P, L100E/I/N/P/V, F101D/H/N/Y, Y102A/K/N/P/V, N103A/D/E/P, E104L/V, Q105P/T, and F106H.

Further, the TCR of the present disclosure is an αβ heterodimeric TCR, and the α chain variable domain of the TCR comprises an amino acid sequence having at least 90%, preferably at least 92%, more preferably at least 94% (e.g., may be at least 90%, 91%, 92%, 93%, 94%, 95%, 96%, 97%, 98%, 99% of sequence homology) of sequence homology with the amino acid sequence as shown in SEQ ID NO: 1; and/or the β chain variable domain of the TCR comprises an amino acid sequence having at least 90%, preferably at least 92%, more preferably at least 94% (e.g., may be at least 91%, 92%, 93%, 94%, 95%, 96%, 97%, 98%, 99% of sequence homology) of sequence homology with the amino acid sequence as shown in SEQ ID NO: 2.

Further, the TCR of the present disclosure is a single-chain TCR, and the α chain variable domain of the TCR comprises an amino acid sequence having at least 85%, preferably at least 90%, more preferably at least 92%, most preferably at least 94% (e.g., may be at least 88%, 89%, 90%, 91%, 92%, 93%, 94%, 95%, 96%, 97%, 98%, 99% of sequence homology) of sequence homology with the amino acid sequence as shown in SEQ ID NO: 3; and/or the β chain variable domain of the TCR comprises an amino acid sequence having at least 85%, preferably at least 90%, more preferably at least 92, most preferably at least 94% (e.g., may be at least 91%, 92%, 93%, 94%, 95%, 96%, 97%, 98%, 99% of sequence homology) of sequence homology with the amino acid sequence as shown in SEQ ID NO: 4.

Preferably, the TCR comprises (i) all or part of a TCR α chain other than its transmembrane domain, and (ii) all or part of a TCR β chain other than its transmembrane domain, wherein both of (i) and (ii) comprise a variable domain and at least a part of the constant domain of the TCR chain.

According to the site-directed mutagenesis method well known to a skilled person in the art, Thr48 of the α chain constant region TRAC*01 exon 1 of the wild-type TCR was mutated to cysteine, and Ser57 of the β chain constant region TRBC1*01 or TRBC2*01 exon 1 was mutated to cysteine, so as to obtain a reference TCR, the amino acid sequences of which are SEQ ID NO: 11 and SEQ ID NO:12, respectively, as shown in FIGS. 6*a* and 6*b*, wherein the mutated cysteine residues are indicated by bold letters. The above cysteine substitutions can form an artificial interchain disulfide bond between the α chain constant region of and the 0 chain constant region of the reference TCR to form a more stable soluble TCR, so that it is easier to evaluate the binding affinity and/or binding half-life between TCR and KASEKIFYV (SEQ ID NO: 29)-HLA A0201 complex. It will be appreciated that the CDR regions of the TCR variable region determine its affinity for pMHC complex, and therefore, the above cysteine substitutions in the TCR constant region won't affect the binding affinity and/or binding half-life of the TCR. Therefore, in the present disclosure, the measured binding affinity between the reference TCR and KASEKIFYV (SEQ ID NO: 29)-HLA A0201 complex is considered to be the binding affinity between the wild-type TCR and KASEKIFYV (SEQ ID NO: 29)-HLA A0201 complex. Similarly, if the binding affinity between the TCR of the present disclosure and KASEKIFYV (SEQ ID NO: 29)-HLA A0201 complex is determined to be at least 10 times the binding affinity between the reference TCR and KASEKIFYV (SEQ ID NO: 29)-HLA A0201 complex, the binding affinity between the TCR of the present disclosure and KASEKIFYV (SEQ ID NO: 29)-HLA A0201 complex is at least 10 times the binding affinity between the wild-type TCR and KASEKIFYV (SEQ ID NO: 29)-HLA A0201 complex.

The binding affinity (in inverse proportion to the dissociation equilibrium constant $K_D$) and the binding half-life (expressed as $T_{1/2}$) can be determined by any suitable method. For example, the detection is performed using surface plasmon resonance technology. It should be understood that doubling of the affinity of the TCR will halve $K_D$. $T_{1/2}$ is calculated as In2 divided by dissociation rate ($K_{off}$). Therefore, doubling of $T_{1/2}$ will halve $K_{off}$. Preferably, the binding affinity or binding half-life of a given TCR is detected for several times by using the same test protocol, for example 3 or more times, and the average of the results is taken. In a preferred embodiment, the affinity of the soluble TCR is detected under the conditions of a temperature of 25° C. and a pH of 7.1-7.5 by a surface plasmon resonance (BIAcore) method in the Examples herein. The dissociation equilibrium constant $K_D$ of the reference TCR to KASEKIFYV (SEQ ID NO: 29)-HLA A0201 complex is detected as 1.21E-04M, that is, 121 μM by the method. In the present disclosure, the dissociation equilibrium constant $K_D$ of the wild-type TCR to KASEKIFYV (SEQ ID NO: 29)-HLA A0201 complex is also considered as 121 μM. Since doubling of the affinity of the TCR will halve $K_D$, if the dissociation equilibrium constant $K_D$ of the high-affinity TCR to KASEKIFYV (SEQ ID NO: 29)-HLA A0201 complex is detected as 1.21E-05M, that is, 12.1 μM, the affinity of the high-affinity TCR for KASEKIFYV (SEQ ID NO: 29)-HLA A0201 complex is 10 times that of the wild-type TCR for KASEKIFYV (SEQ ID NO: 29)-HLA A0201 complex. A skilled person is familiar with the conversion relationship between $K_D$ value units, i.e., 1 M=$10^6$ μM, 1 μM=1000 nM, and 1 nM=1000 pM.

In another preferred embodiment of the present disclosure, the affinity of the TCR for KASEKIFYV (SEQ ID NO: 29)-HLA A0201 complex is at least twice, preferably at least five times, more preferably at least ten times that of the wild-type TCR.

In another preferred embodiment, the affinity of the TCR for KASEKIFYV (SEQ ID NO: 29)-HLA A0201 complex is at least 50 times, preferably at least 100 times, more preferably at least 300 times that of the wild-type TCR.

In particular, the dissociation equilibrium constant $K_D$ of the TCR to KASEKIFYV (SEQ ID NO: 29)-HLA A0201 complex is ≤60 μM.

In another preferred embodiment, the dissociation equilibrium constant of the TCR to KASEKIFYV (SEQ ID NO: 29)-HLA A0201 complex is 1 μM≤$K_D$≤50 μM.

Mutations can be carried out by any suitable method including, but not limited to, those based on the polymerase chain reaction (PCR), restriction enzyme-based cloning or a linkage-independent cloning (LIC) method. These methods are described in detail in many standard molecular biology textbooks. More details about polymerase chain reaction (PCR) mutagenesis and restriction enzyme-based cloning can be found in Sambrook and Russell, (2001) Molecular Cloning-A Laboratory Manual (Third Edition) CSHL Publishing house. More information about the LIC method can be found in Rashtchian, (1995) Curr Opin Biotechnol 6(1): 30-6.

A method for producing the TCR of the present disclosure may be, but not limited to, screening a TCR having high affinity for KASEKIFYV (SEQ ID NO: 29)-HLA-A0201 complex from a diverse library of phage particles displaying such TCRs, as described in a literature (Li, et al. (2005) Nature Biotech 23(3): 349-354).

It will be appreciated that genes expressing amino acids of α and β chain variable domains of the wild type TCR or genes expressing amino acids of α and β chain variable domains of a slightly modified wild type TCR can both be used for preparing template TCRs. Changes necessary to produce the high affinity TCR of the present disclosure are then introduced into the DNA encoding the variable domain of the template TCR.

In the present disclosure, the amino acid sequences of the α chain variable domain and the β chain variable domain which form the heterodimeric TCR molecule are preferably selected from Table 1.

TABLE 1

| TCR No. | Sequence of α chain variable domain SEQ ID NO: | Sequence of β chain variable domain SEQ ID NO: |
|---|---|---|
| 1 | 1 | 13 |
| 2 | 1 | 14 |
| 3 | 1 | 15 |
| 4 | 1 | 16 |
| 5 | 1 | 17 |
| 6 | 1 | 18 |
| 7 | 1 | 19 |
| 8 | 1 | 20 |
| 9 | 1 | 21 |
| 10 | 1 | 22 |
| 11 | 1 | 23 |
| 12 | 1 | 24 |

Based on the object of the present disclosure, the TCR of the present disclosure is a moiety having at least one TCR α and/or TCR β chain variable domain. Such TCRs generally comprise both the TCR α chain variable domain and the TCR β chain variable domain. They may be αβ heterodimers or in a single chain form or any other stable forms. In adoptive immunotherapy, the full length chain of the αβ heterodimeric TCR (including the cytoplasmic and transmembrane domains) can be transfected. The TCR of the present disclosure can be used as a targeting agent for delivering a therapeutic agent to an antigen-presenting cell or be used in combination with other molecules to prepare a bifunctional polypeptide to direct effector cells when the TCR is preferably in a soluble form.

As for stability, it is disclosed in the existing art that a soluble and stable TCR molecule can be obtained by introducing an artificial interchain disulfide bond between the α and β chain constant domains of a TCR, as described in PCT/CN2015/093806. Therefore, the TCR of the present disclosure may be a TCR with an artificial interchain disulfide bond introduced between the residues of its α and β chain constant domains. Cysteine residues form an artificial interchain disulfide bond between the α and β chain constant domains of the TCR. Cysteine residues can replace other amino acid residue at suitable positions of a native TCR to form an artificial interchain disulfide bond. For example, Thr48 of TRAC*01 exon 1 and Ser57 of TRBC1*01 or TRBC2*01 exon 1 can be replaced to form a disulfide bond. Other sites for introducing a cysteine residue to form a disulfide bond may be: Thr45 of TRAC*01 exon 1 and Ser77 of TRBC1*01 or TRBC2*01 exon 1; Tyr10 of TRAC*01 exon 1 and Ser17 of TRBC1*01 or TRBC2*01 exon 1; Thr45 of TRAC*01 exon 1 and Asp59 of TRBC1*01 or TRBC2*01 exon 1; Ser15 of TRAC*01 exon 1 and Glu15 of TRBC1*01 or TRBC2*01 exon 1; Arg53 of TRAC*01 exon 1 and Ser54 of TRBC1*01 or TRBC2*01 exon 1; Pro89 of TRAC*01 exon 1 and Ala19 of TRBC1*01 or TRBC2*01 exon 1; or Tyr10 of TRAC*01 exon 1 and Glu20 of TRBC1*01 or TRBC2*01 exon 1. That is, cysteine residues replace any group of the above-mentioned sites in a and β chain constant domains. A maximum of 15, or a maximum of 10, or a maximum of 8 or fewer amino acids may be truncated at one or more C-termini of the constant domain of the TCR of the present disclosure such that it does not include cysteine residues to achieve the purpose of deleting a natural interchain disulfide bond, or the cysteine residues forming a natural interchain disulfide bond can also be mutated to another amino acid for achieving the above purpose.

As described above, the TCR of the present disclosure may comprise an artificial interchain disulfide bond introduced between residues of its α and β chain constant domains. It is to be noted that the introduced artificial disulfide bond as described above can be contained or not contained between the constant domains, and the TCR of the present disclosure may contain a TRAC constant domain sequence and a TRBC1 or TRBC2 constant domain sequence. The TRAC constant domain sequence and the TRBC1 or TRBC2 constant domain sequence of the TCR can be linked by a natural interchain disulfide bond present in the TCR.

Additionally, as for stability, it is also disclosed in a patent literature PCT/CN2016/077680 that the introduction of an artificial interchain disulfide bond between the α chain variable region and the β chain constant region of a TCR can significantly improve the stability of the TCR. Therefore, an artificial interchain disulfide bond may be contained between an α chain variable region and a β chain constant region of the high affinity TCR of the present disclosure. Specifically, cysteine residues forming an artificial interchain disulfide bond between the α chain variable region and the β chain constant region of the TCR replace: an amino acid at position 46 of TRAV and an amino acid at position 60 of TRBC1*01 or TRBC2*01 exon 1; an amino acid at position 47 of TRAV and an amino acid at position 61 of TRBC1*01 or TRBC2*01 exon 1; an amino acid at position 46 of TRAV and an amino acid at position 61 of TRBC1*01 or TRBC2*01 exon 1; or an amino acid at position 47 of TRAV and an amino acid at position 60 of TRBC1*01 or TRBC2*01 exon 1. Preferably, such a TCR may comprise (i) all or part of a TCR α chain other than its transmembrane domain and (ii) all or part of a TCR β chain other than its transmembrane domain, wherein both of (i) and (ii) comprise a variable domain and at least part of a constant domain of the TCR chain, and the α chain and the β chain form a heterodimer. More preferably, such TCR may comprise an α chain variable domain, a β chain variable domain and all or part of a β chain constant domain other than the transmembrane domain, which, however, does not comprise an α chain constant domain, and the α chain variable domain and the β chain of the TCR form a heterodimer.

As for stability, in another aspect, the TCR of the present disclosure also includes a TCR having a mutation in its hydrophobic core region, and these mutations in the hydrophobic core region are preferably mutations capable of increasing the stability of the TCR of the present disclosure, as described in WO 2014/206304. Such a TCR can have mutations at the following positions in the variable domain hydrophobic core: (α and/or β chain) variable region amino acids at positions 11, 13, 19, 21, 53, 76, 89, 91, 94 and/or α chain J gene (TRAJ) short peptide amino acids at reciprocal positions 3, 5, 7 and/or β chain J gene (TRBJ) short peptide amino acids at reciprocal positions 2, 4, 6, wherein the positions in an amino acid sequence are numbered according to the position numbers listed in the International ImMunoGeneTics Information System (IMGT). Those skilled in the art know the preceding IMGT and can obtain the position numbers of amino acid residues of different TCRs in the IMGT based on the database.

More specifically, in the present disclosure, a TCR having a mutation in its hydrophobic core region may be a high-stability single chain TCR consisting of TCR α and β chain variable domains linked by a flexible peptide chain. CDRs in the variable region of the TCR determine the affinity of the TCR for a short peptide-HLA complex, and mutations in a hydrophobic core can increase the stability of the TCR without affecting the affinity of the TCR for the short peptide-HLA complex. It is to be noted that the flexible peptide chain in the present disclosure may be any peptide chain suitable for linking TCR α and β chain variable domains. A template chain constructed in Example 1 of the present disclosure for screening high affinity TCRs is the preceding high-stability single chain TCR containing mutations in the hydrophobic core. The affinity between a TCR and KASEKIFYV (SEQ ID NO: 29)-HLA-A0201 complex can be more easily evaluated by using a TCR with higher stability.

The CDR regions of the α chain variable domain and the β chain variable domain of the single-chain template TCR are identical to the CDR regions of the wild-type TCR. That is, the three CDRs of the α chain variable domain are CDR1α: TSESDYY (SEQ ID NO: 31), CDR2α: QEAYKQQN (SEQ ID NO: 32), and CDR3α: AYRSGIIQGAQKLV (SEQ ID NO: 30), and the three CDRs of the β chain variable domains are CDR1β: PRHDT (SEQ ID NO: 33), CDR2β: FYEKMQ (SEQ ID NO: 34), and CDR3β: ASSSDRELLFYNEQF (SEQ ID NO: 38), respectively. The amino acid sequence (SEQ ID NO: 9) and nucleotide sequence (SEQ ID NO: 10) of the single-chain template TCR are shown in FIGS. 5*a* and 5*b*, respectively, thereby screening a single-chain TCR consisting of an α chain variable domain and a β chain variable domain and having high affinity for KASEKIFYV (SEQ ID NO: 29)-HLA A0201 complex.

In the present disclosure, the three CDRs of the α chain variable domain of the single-chain template TCR (SEQ ID NO: 3), i.e., CDR1, CDR2 and CDR3, are located at positions 27-33, 51-58 and 93-106 of SEQ ID NO: 1, respectively.

In the present disclosure, the three CDRs of the (3 chain variable domain of the single-chain template TCR (SEQ ID NO: 4), i.e., CDR1, CDR2 and CDR3, are located at positions 27-31, 49-54 and 92-106 of SEQ ID NO: 2, respectively. Accordingly, amino acid residues are numbered as shown in SEQ ID NO: 4, 96D is D at position 5 of CDR3β, 98E is E at position 7 of CDR3β, 99L is L at position 8 of CDR3β, 100L is L at position 9 of CDR3β, 101F is F at position 10 of CDR11β, 102Y is Y at position 11 of CDR3β, 103N is N at position 12 of CDR3β, 104E is E at position 13 of CDR3β, 105Q is Q at position 14 of CDR3β, and 106F is F at position 15 of CDR3β.

The αβ heterodimer of the present disclosure having high affinity for KASEKIFYV (SEQ ID NO: 29)-HLA-A0201 complex is obtained by transferring the CDR regions of α and β chain variable domains of the selected high-affinity single-chain TCR to the corresponding positions of the α chain variable domain (SEQ ID NO: 1) and the β chain variable domain (SEQ ID NO: 2) of a wild-type TCR.

The TCR of the present disclosure can also be provided in the form of a multivalent complex. The multivalent TCR complex of the present disclosure comprises a polymer formed by combining two, three, four or more TCRs of the present disclosure, for example, a tetrameric domain of p53 can be used to produce a tetramer. Alternatively, multiple TCRs of the present disclosure can be combined with another molecule to form a complex. The TCR complex of the present disclosure can be used to track or target cells that present a particular antigen in vitro or in vivo or produce intermediates of other multivalent TCR complexes with such uses.

The TCR of the present disclosure may be used alone or combined with a conjugate in a covalent manner or another manner, preferably in the covalent manner. The conjugate includes a detectable label (for diagnostic purposes, wherein the TCR is used to detect the presence of a cell presenting KASEKIFYV (SEQ ID NO: 29)-HLA-A0201 complex), a therapeutic agent, a protein kinase (PK) modified moiety or a combination of any of the preceding substances.

Detectable labels for diagnostic purposes include, but are not limited to, fluorescent or luminescent labels, radioactive labels, magnetic resonance imaging (MM) or electron computed tomography (CT) contrast agents or enzymes capable of producing detectable products.

Therapeutic agents that can be combined with or coupled to the TCR of the present disclosure include, but are not limited to: 1. radionuclides (Koppe et al., 2005, Cancer metastasis reviews 24, 539); 2. biotoxin (Chaudhary et al., 1989, Nature 339, 394; Epel et al., 2002, Cancer Immunology and Immunotherapy 51, 565); 3. cytokines such as IL-2 (Gillies et al., 1992, *Proceedings of the National Academy of Sciences of the United States of America* (PNAS) 89, 1428; Card et al., 2004, Cancer Immunology and Immunotherapy 53, 345; Halin et al., 2003, Cancer Research 63, 3202); 4. antibody Fc fragments (Mosquera et al., 2005, the Journal Of Immunology 174, 4381); 5. antibody scFv fragments (Zhu et al., 1995, International Journal of Cancer 62, 319); 6. gold nanoparticles/nanorods (Lapotko et al., 2005, Cancer letters 239, 36; Huang et al., 2006, Journal of the American Chemical Society 128, 2115); 7. viral particles (Peng et al., 2004, Gene therapy 11, 1234); 8. liposomes (Mamot et al., 2005, Cancer research 65, 11631); 9. nanomagnetic particles; 10. prodrug activating enzymes (e.g., DT-diaphorase (DTD) or biphenyl hydrolase-like protein (BPHL); 11. chemotherapeutic agents (e.g., cisplatin) or any form of nanoparticles, and the like.

An antibody binding to the TCR of the present disclosure or a fragment thereof includes an anti-T cell or an NK-cell determining antibody, such as an anti-CD3 or anti-CD28 or anti-CD16 antibody. The above antibody or a fragment thereof binds to the TCR, which can direct effector cells to better target target cells. In a preferred embodiment, the TCR of the present disclosure binds to an anti-CD3 antibody or a functional fragment or variant thereof. Specifically, a fusion molecule of the TCR of the present disclosure and an anti-CD3 single chain antibody comprises a TCR α chain variable domain whose amino acid sequence is SEQ ID NOs: 1 and/or a TCR chain variable domain whose amino acid sequence is any one of SEQ ID NOs: 13-24.

The present disclosure further relates to a nucleic acid molecule encoding the TCR of the present disclosure. The nucleic acid molecule of the present disclosure may be in the form of DNA or RNA. DNA may be a coding strand or a non-coding strand. For example, a nucleic acid sequence encoding the TCR of the present disclosure may be the same as the nucleic acid sequence shown in the Figures of the present disclosure or a degenerate variant thereof. By way of example, the "degenerate variant", as used herein, refers to a nucleic acid sequence which encodes a protein with a sequence of SEQ ID NO: 9 but is different from the sequence of SEQ ID NO: 10.

The full length sequence of the nucleic acid molecule of the present disclosure or a fragment thereof may generally be obtained by, but not limited to, a PCR amplification method, a recombination method or an artificial synthesis method. At present, it has been possible to obtain a DNA sequence encoding the TCR (or a fragment thereof or a derivative thereof) of the present disclosure completely by chemical synthesis. Then, the DNA sequence can be introduced into various existing DNA molecules (or vectors) and cells known in the art.

The present disclosure further relates to a vector comprising the nucleic acid molecule of the present disclosure as well as a host cell genetically engineered using the vector or coding sequence of the present disclosure.

The present disclosure further encompasses an isolated cell, particularly a T cell, which express the TCR of the present disclosure. There are many methods suitable for T cell transfection with DNA or RNA encoding the high affinity TCR of the present disclosure (e.g., Robbins et al., (2008) J. Immunol. 180: 6116-6131). T cells expressing the high affinity TCR of the present disclosure can be used for adoptive immunotherapy. Those skilled in the art can know many suitable methods for adoptive therapy (e.g., Rosenberg et al., (2008) Nat Rev Cancer 8(4): 299-308).

The present disclosure further provides a pharmaceutical composition, which comprise a pharmaceutically acceptable carrier and the TCR of the present disclosure or the TCR complex of the present disclosure or the cell presenting the TCR of the present disclosure.

The present disclosure further provides a method for treating a disease, which comprises administering a subject to be treated with an appropriate amount of the TCR of the present disclosure or the TCR complex of the present disclosure or the cell presenting the TCR of the present disclosure or the pharmaceutical composition of the present disclosure.

It is to be understood that amino acid names herein are identified by internationally accepted single English letters, and the corresponding three-letter abbreviated names of amino acids are: Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y), Val (V).

In the present disclosure, both of Pro60 or 60P represent proline at position 60. Further, regarding the expression of the specific form of mutation in the present disclosure, for example, "D96V" represents that D at position 96 is substituted by V, similarly, "E104L/V" means that E at position 104 is substituted by L or substituted by V, and so on.

In the art, when an amino acid with similar properties is used for substitution, the function of a protein is generally not changed. The addition of one amino acid or multiple amino acids at C-terminal and/or N-terminal generally will not change the structure and function of the protein. Therefore, the TCR of the present disclosure further includes a TCR wherein up to 5, preferably up to 3, more preferably up to 2, most preferably 1 amino acid (especially an amino acid located outside CDRs) of the TCR of the present disclosure is replaced with an amino acid with similar properties and which can still maintain its function.

The present disclosure further includes a TCR slightly modified from the TCR of the present disclosure. The form of a modification (generally without altering a primary structure) includes chemically derived forms of the TCR of the present disclosure, such as acetylation or carboxylation. Modifications also include glycosylation, such as those TCRs produced through glycosylation in the synthesis and processing steps or in the further processing step of the TCR of the present disclosure. Such modification can be accomplished by exposing the TCR to an enzyme for glycosylation (such as a mammalian glycosylation enzyme or a deglycosylation enzyme). The form of the modification further includes sequences having phosphorylated amino acid residues (such as phosphotyrosine, phosphoserine and phosphothreonine). Further included are TCRs that have been modified to enhance their antiproteolytic properties or optimize solubility properties.

The TCR or TCR complex of the present disclosure or the T cell transfected with the TCR of the present disclosure may be provided in a pharmaceutical composition together with a pharmaceutically acceptable carrier. The TCR, multivalent TCR complex or cell of the present disclosure is typically provided as part of a sterile pharmaceutical composition which typically comprises a pharmaceutically acceptable carrier. The pharmaceutical composition may be in any suitable form (depending on the desired method for administration to a patient). The pharmaceutical composition may be provided in a unit dosage form, generally provided in a sealed container and may be provided as part of a kit. Such kits include instructions (which are not necessary). The pharmaceutical composition may include multiple unit dosage forms.

Furthermore, the TCR of the present disclosure may be used alone or in combination with other therapeutic agents (e.g., formulated in the same pharmaceutical composition).

The pharmaceutical composition may also contain a pharmaceutically acceptable carrier. The term "pharmaceutically acceptable carrier" refers to a carrier for administration of a therapeutic agent. The term refers to such pharmaceutical carriers which do not induce the production of antibodies harmful to an individual receiving the composition and which are not excessively toxic after administration. These carriers are well known to those skilled in the art. A full discussion of pharmaceutically acceptable excipients can be found in Remington's Pharmaceutical Sciences (Mack Pub.

Co., N. J. 1991). Such carriers include, but are not limited to, saline, buffer, dextrose, water, glycerol, ethanol, adjuvants and combinations thereof.

The pharmaceutically acceptable carrier in the therapeutic composition may contain a liquid such as water, saline, glycerol and ethanol. In addition, auxiliary substances such as wetting or emulsifying agents and pH buffering substances may also be present in these carriers.

Generally, the therapeutic compositions may be formulated as injectables such as liquid solutions or suspensions and may also be formulated as solid forms such as liquid carriers, which may be suitable for being formulated in solutions or suspensions prior to injection.

Once the composition of the present disclosure is formulated, it may be administered by conventional routes including, but not limited to, intraocular, intramuscular, intravenous, subcutaneous, intradermal or topical administration, preferably parenteral administration including subcutaneous, intramuscular or intravenous administration. A subject to be prevented or treated may be an animal, especially a human.

When the pharmaceutical composition of the present disclosure is used for actual treatment, pharmaceutical compositions of various dosage forms may be employed depending on uses, preferably, an injection, an oral preparation or the like.

These pharmaceutical compositions may be formulated by being mixed, diluted or dissolved by conventional methods and, occasionally, be added with suitable pharmaceutical additives such as excipients, disintegrating agents, binders, lubricants, diluents, buffers, isotonicities, preservatives, wetting agents, emulsifiers, dispersing agents, stabilizers and co-solvents, and the formulation process may be carried out in a customary manner depending on the dosage form.

The pharmaceutical composition of the present disclosure may also be administered in the form of a sustained release preparation. For example, the TCR of the present disclosure may be incorporated into a pill or microcapsule with a sustained release polymer as a carrier and then the pill or microcapsule is surgically implanted into the tissue to be treated. Examples of the sustained release polymer include ethylene-vinyl acetate copolymer, polyhydrometaacrylate, polyacrylamide, polyvinylpyrrolidone, methylcellulose, lactic acid polymer, lactic acid-glycolic acid copolymer or the like, preferably a biodegradable polymer such as lactic acid polymer and lactic acid-glycolic acid copolymer.

When the pharmaceutical composition of the present disclosure is used for actual treatment, the amount of the TCR or TCR complex of the present disclosure or the cell presenting the TCR of the present disclosure as an active ingredient may be reasonably determined by a doctor based on the body weight, age, sex and degree of symptoms of each patient to be treated.

Main Advantages of the Present Disclosure (1) The affinity and/or binding half-life of the TCR of the present disclosure for KASEKIFYV (SEQ ID NO: 29)-HLA-A0201 complex is at least twice, preferably at least 10 times that of a wild-type TCR.
(2) The affinity and/or binding half-life of the TCR of the present disclosure for KASEKIFYV (SEQ ID NO: 29)-HLA-A0201 complex is at least 50 times, preferably at least 100 times, and more preferably up to 300 times that of a wild-type TCR.
(3) Effector cells transduced with the high-affinity TCR of the present disclosure exhibit a strong killing effect on target cells.

The present disclosure is further illustrated by the following specific examples. It is to be understood that these examples are used only for the purpose of illustration and not intended to limit the scope of the present disclosure. Experimental methods in the following examples which do not specify specific conditions are generally performed under conventional conditions, for example, conditions described in Sambrook and Russell et al., Molecular Cloning-A Laboratory Manual (Third Edition) (2001) CSHL Publishing house or under conditions recommended by the manufacturer. Percentages and parts are by weight unless otherwise stated.

Materials and Methods

The experimental materials used in the examples of the present disclosure may be commercially available, unless otherwise specified, where *E. coli* DH5a was purchased from Tiangen, *E. coli* BL21 (DE3) was purchased from Tiangen, *E. coli* Tuner (DE3) was purchased from Novagen, and plasmid pET28a was purchased from Novagen.

Example 1 Generation of Stable Single Chain TCR Template Chains with Mutations in the Hydrophobic Core In the present disclosure, a stable single chain TCR molecule consisting of TCR α and β chain variable domains linked by a flexible short peptide (linker) was constructed by a site-directed mutagenesis method according to a patent literature WO2014/206304, where the amino acid sequence and DNA sequence thereof are SEQ ID NO: 9 and SEQ ID NO: 10, respectively, as shown in FIGS. 5*a* and 5*b*. The single chain TCR molecule was used as a template for screening a high affinity TCR molecule. The amino acid sequences of an α variable domain (SEQ ID NO: 3) and a β variable domain (SEQ ID NO: 4) of the template chain are shown in FIGS. 2*a* and 2*b*; the corresponding DNA sequences are SEQ ID NO: 5 and SEQ ID NO: 6, respectively, as shown in FIGS. 3*a* and 3*b*; and the amino acid sequence and DNA sequence of the flexible short peptide (linker) are SEQ ID NO: 7 and SEQ ID NO: 8, respectively, as shown in FIGS. 4*a* and 4*b*.

The target gene carrying the template chain was digested with NcoI and NotI and ligated with pET28a vector digested with NcoI and NotI. The ligation product was transferred into *E. coli* DH5a, plated on a kanamycin-containing LB plate, inverted and cultured at 37° C. overnight, and the positive clones were picked for PCR screening. Positive recombinants were sequenced to determine the correct sequence and the recombinant plasmid was extracted and transferred into *E. coli* BL21 (DE3) for expression.

Example 2 Expression, Refolding and Purification of the Stable Single Chain TCR Constructed in Example 1

All of BL21(DE 3) colonies containing the recombinant plasmid pET28a-template chain prepared in Example 1 were inoculated into the LB medium containing kanamycin and cultured at 37° C. until $OD_{600}$ was 0.6-0.8. IPTG was added to a final concentration of 0.5 mM and cultured at 37° C. for another 4 h. The cell pellets were harvested by centrifugation at 5000 rpm for 15 min, and the cell pellets were lysed with Bugbuster Master Mix (Merck). The inclusion bodies were recovered by centrifugation at 6000 rpm for 15 min, followed by washing with Bugbuster (Merck) to remove cell debris and membrane components. The inclusion bodies were collected by centrifugation at 6000 rpm for 15 min. The inclusion bodies were dissolved in a buffer (20 mM Tris-HCl pH 8.0, 8 M urea), and the insoluble substances were removed by high-speed centrifugation. The supernatant was quantitatively determined by the BCA method and then dispensed and stored at −80° C. until use.

To 5 mg of dissolved single-chain TCR inclusion body protein, 2.5 mL of buffer (6 M Gua-HCl, 50 mM Tris-HCl pH 8.1, 100 mM NaCl, 10 mM EDTA) was added, and then DTT was added to a final concentration of 10 mM and incubated at 37° C. for 30 min. The single chain TCR as treated above was added dropwise to 125 mL of refolding buffer (100 mM Tris-HCl pH 8.1, 0.4 M L-arginine, 5 M urea, 2 mM EDTA, 6.5 mM β-mercapthoethylamine, 1.87 mM cystamine) with a syringe and stirred at 4° C. for 10 min. Then the refolded solution was loaded into a cellulose membrane dialysis bag with a cut-off of 4 kDa, and the dialysis bag was placed in 1 L of pre-cooled water and stirred slowly at 4° C. overnight. After 17 h, the dialysis liquid was changed to 1 L of pre-chilled buffer (20 mM Tris-HCl pH 8.0) and dialysis was continued for 8 h at 4° C. The dialysis liquid was then replaced with the same fresh buffer and dialysis was continued overnight. After 17 h, the sample was filtered through a 0.45 μm filter, vacuum degassed and purified through an anion exchange column (HiTrap Q HP, GE Healthcare) with a linear gradient elution of 0-1 M NaCl prepared with 20 mM Tris-HCl pH 8.0. The collected fractions were subjected to SDS-PAGE analysis, the fractions containing the single chain TCR were concentrated and further purified by a gel filtration column (Superdex 75 10/300, GE Healthcare), and the target fractions were also subjected to the SDS-PAGE analysis.

The eluted fractions for BIAcore analysis were further tested using gel filtration for purity. The conditions were a chromatographic column Agilent Bio SEC-3 (300 A, φ7.8×300 mm), a mobile phase 150 mM phosphate buffer, a flow rate of 0.5 mL/min, a column temperature of 25° C., and a UV detection wavelength of 214 nm.

Example 3 Binding Characterization

BIAcore Analysis

The binding activity of a TCR molecule to KASEKIFYV (SEQ ID NO: 29)-HLA-A0201 complex was detected using the BIAcore T200 real-time analysis system. An anti-streptavidin antibody (GenScript) was added to a coupling buffer (10 mM sodium acetate buffer, pH 4.77), and then the antibody passed through a CMS chip pre-activated with EDC and NHS to immobilize the antibody on the surface of the chip. The unreacted activated surface was finally blocked with a solution of ethanolamine in hydrochloric acid to complete the coupling process at a coupling level of about 15000 RU. The conditions were a temperature of 25° C. and a pH of 7.1-7.5.

Streptavidin with a low concentration flowed over the surface of the antibody-coated chip, and then KASEKIFYV (SEQ ID NO: 29)-HLA-A0201 complex flowed through the detection channel with another channel as a reference channel. 0.05 mM biotin flowed over the chip for 2 min at a flow rate of 10 μL/min, thereby blocking the remaining binding sites for streptavidin. The affinity was determined by a single-cycle kinetic analysis. The TCR was diluted to several different concentrations with HEPES-EP buffer (10 mM HEPES, 150 mM NaCl, 3 mM EDTA, 0.005% P20, pH 7.4) and flowed over the surface of the chip in sequence at a flow rate of 30 μL/min, with a binding time of 120 s per injection. After the last injection, the chip was placed for dissociation for 600 s. At the end of each round of assay, the chip was regenerated with 10 mM Gly-HCl, pH 1.75. Kinetic parameters were calculated using BIAcore Evaluation software.

The preparation process of the preceding KASEKIFYV (SEQ ID NO: 29)-HLA-A0201 complex is described below.

a. Purification 100 mL of *E. coli* liquid induced to express heavy or light chains was collected and centrifuged at 8000 g for 10 min at 4° C., and the cells were washed once with 10 mL of PBS and then vigorously shaken in 5 mL of BugBuster Master Mix Extraction Reagents (Merck) for resuspending the cells. The suspension was incubated for 20 min at room temperature and then centrifuged at 6000 g for 15 min at 4° C. The supernatant was discarded to collect inclusion bodies.

The above inclusion bodies were resuspended in 5 mL of BugBuster Master Mix and incubated vortically at room temperature for 5 min. 30 mL of BugBuster diluted 10 times was added, mixed and centrifuged at 6000 g for 15 min at 4° C. The supernatant was discarded, and 30 mL of BugBuster diluted 10 times was added to resuspend the inclusion bodies, mixed and centrifuged twice at 6000 g at 4° C. for 15 min. 30 mL of 20 mM Tris-HCl pH 8.0 was added to resuspend the inclusion bodies, mixed and centrifuged at 6000 g at 4° C. for 15 min. Finally, the inclusion bodies were dissolved in 20 mM Tris-HCl 8M urea. The purity of the inclusion bodies was determined by SDS-PAGE and the concentration was measured by the BCA kit.

b. Refolding

The synthesized short peptide KASEKIFYV (SEQ ID NO: 29) (Beijing Saibaisheng Gene Technology Co., Ltd.) was dissolved in DMSO to a concentration of 20 mg/mL. Inclusion bodies of light and heavy chains were solubilized in 8 M urea, 20 mM Tris pH 8.0, 10 mM DTT and further denatured by adding 3 M guanidine hydrochloride, 10 mM sodium acetate, 10 mM EDTA before refolding. KASEKIFYV (SEQ ID NO: 29) peptide was added to a refolding buffer (0.4 M L-arginine, 100 mM Tris pH 8.3, 2 mM EDTA, 0.5 mM oxidized glutathione, 5 mM reduced glutathione, 0.2 mM PMSF, cooled to 4° C.) at 25 mg/L (final concentration). Then, 20 mg/L of light chain and 90 mg/L of heavy chain (final concentration, heavy chains were added in three portions, 8 h/portion) were successively added and refolded at 4° C. for at least three days to completion of refolding, and SDS-PAGE was used to confirm refolding.

c. Purification Upon Refolding

The refolding buffer was replaced with 10 volumes of 20 mM Tris pH 8.0 for dialysis, and the buffer was replaced at least twice to fully reduce the ionic strength of the solution. After dialysis, the protein solution was filtered through a 0.45 μm cellulose acetate filter and loaded onto a HiTrap Q HP (GE, General Electric Company) anion exchange column (5 mL bed volume). The protein was eluted with a linear gradient of 0-400 mM NaCl prepared in 20 mM Tris pH 8.0 using Akta Purifier (GE), and pMHC was eluted at approximately 250 mM NaCl. Peak fractions were collected and the purity thereof was detected by SDS-PAGE.

d. Biotinylation

Purified pMHC molecules were concentrated in a Millipore ultrafiltration tube while the buffer was replaced with 20 mM Tris pH 8.0. Then, biotinylation reagents 0.05 M Bicine pH 8.3, 10 mM ATP, 10 mM MgOAc, 50 μM D-Biotin, 100 μg/ml BirA enzyme (GST-BirA) were added.

The resulting mixture was incubated at room temperature overnight, and SDS-PAGE was used to detect the completion of biotinylation.

e. Purification of the Biotinylated Complex

The biotinylated and labeled pMHC molecules were concentrated to 1 mL in the Millipore ultrafiltration tube. The biotinylated pMHC was purified by gel permeation chromatography. 1 mL of concentrated biotinylated pMHC molecules was loaded on a HiPrep™ 16/60 S200 HR column (GE) pre-equilibrated with filtered PBS using Akta Purifier (GE) and eluted with PBS at a flow rate of 1 mL/min. The biotinylated pMHC molecules were eluted as a single peak at about 55 mL. The protein-containing fractions were combined and concentrated in the Millipore ultrafiltration tube. The concentration of proteins was determined by the BCA method (Thermo), a protease inhibitor cocktail (Roche) was added and the biotinylated pMHC molecules were dispensed and stored at −80° C.

Example 4 Generation of a High Affinity TCR

Phage display technology is a means to generate high affinity TCR variant libraries for screening high affinity variants. The TCR phage display and screening method described by Li et al. ((2005) Nature Biotech 23(3): 349-354) was applied to the single chain TCR template in Example 1. A library of high affinity TCRs was established by mutating CDRs of the template chain and panned. After several rounds of panning, the phage library can specifically bind to the corresponding antigen, a monoclone was picked, and a sequence analysis was performed.

The mutations in CDRs of the obtained high affinity single chain TCRs were introduced into the corresponding sites of the variable domains of the αβ heterodimeric TCR, and the affinity of the αβ heterodimeric TCR for KASEKIFYV (SEQ ID NO: 29)-HLA-A0201 complex was detected by BIAcore. The mutated sites of high affinity were introduced into the above CDRs by a site-directed mutagenesis method well known to those skilled in the art. The amino acid sequences of α and β chain variable domains of the above wild type TCR are shown in FIG. 1*a* (SEQ ID NO: 1) and 1*b* (SEQ ID NO: 2), respectively.

It is to be noted that to obtain a more stable soluble TCR for easier evaluation of the binding affinity and/or binding half-life between the TCR and KASEKIFYV (SEQ ID NO: 29)-HLA A0201 complex, the αβ heterodimeric TCR may be a TCR in which a cysteine residue is respectively introduced into α and β chain constant domains to form an artificial interchain disulfide bond. In this example, the amino acid sequences of TCR α and β chains after the introduction of the cysteine residue are shown in FIGS. 6*a* (SEQ ID NO: 11) and 6*b* (SEQ ID NO: 12), where the introduced cysteine residues are indicated by bold letters.

According to standard methods described in Molecular Cloning-A Laboratory Manual (Third Edition, Sambrook and Russell), genes of extracellular sequences of TCR α and β chains to be expressed are synthesized and inserted into an expression vector pET28a+ (Novagene) in which the upstream and downstream cloning sites are NcoI and NotI, respectively. Mutations in the CDRs are introduced by overlap PCR well known to those skilled in the art. The inserted fragment was sequenced to confirm that it was correct.

Example 5 Expression, Refolding and Purification of High Affinity TCR

Expression vectors for TCR α and β chains were transferred into the expression bacteria BL21 (DE3) by chemical transformation, respectively. The bacteria were grown in an LB medium and induced with a final concentration of 0.5 mM IPTG at $OD_{600}$=0.6. The inclusion bodies formed after the TCR α and β chains were expressed were extracted by BugBuster Mix (Novagene) and repeatedly washed with a BugBuster solution. The inclusion bodies were finally dissolved in 6 M guanidine hydrochloride, 10 mM dithiothreitol (DTT), 10 mM ethylenediaminetetraacetic acid (EDTA), 20 mM Tris (pH 8.1).

The dissolved TCR α and β chains were rapidly mixed in 5 M urea, 0.4 M arginine, 20 mM Tris (pH 8.1), 3.7 mM cystamine, 6.6 mM β-mercapoethylamine (4° C.) at a mass ratio of 1:1. The final concentration was 60 mg/mL. After mixing, the solution was dialyzed against 10 volumes of deionized water (4° C.). After 12 h, deionized water was replaced with a buffer (20 mM Tris, pH 8.0) and dialysis was continued at 4° C. for 12 h. After completion of the dialysis, the solution was filtered through a 0.45 μM filter and purified through an anion exchange column (HiTrap Q HP, 5 mL, GE Healthcare). The elution peak of the TCR containing the successfully refolded αβ dimer was confirmed by SDS-PAGE gel. The TCR was then further purified by gel permeation chromatography (HiPrep 16/60, Sephacryl S-100 HR, GE Healthcare). The purity of the purified TCR was determined by SDS-PAGE to be greater than 90%, and the concentration thereof was determined by the BCA method.

Example 6. Results of BIAcore Analysis

The affinity of the αβ heterodimeric TCR, in which a high-affinity CDR region was introduced, for KASEKIFYV (SEQ ID NO: 29)-HLA-A0201 complex was detected by using the method described in Example 3.

The amino acid sequences of the β chain variable domains of the high-affinity TCR obtained in the present disclosure are shown in FIGS. 7(1)-(12). Since the CDR regions of a TCR molecule determine their affinity for the corresponding pMHC complex, a skilled person in the art can anticipate that an αβ heterodimeric TCR, in which a high-affinity mutation site is introduced, also has high affinity for KASEKIFYV (SEQ ID NO: 29)-HLA-A0201 complex. The expression vector was constructed by the method described in Example 4, the above-mentioned αβ heterodimeric TCR with a high-affinity mutation being introduced was expressed, refolded and purified by the method described in Example 5, and then the affinity of the TCR for KASEKIFYV (SEQ ID NO: 29)-HLA-A0201 complex is determined by BIAcore T200, as shown in Table 2 below.

TABLE 2

| | TCR variable domain (SEQ ID NO) | | |
|---|---|---|---|
| TCR No. | α | β | $K_D$ (M) |
| 1 | 1 | 13 | 3.00E−05 |
| 2 | 1 | 14 | 4.91E−06 |
| 3 | 1 | 15 | 1.67E−05 |
| 4 | 1 | 16 | 2.58E−05 |
| 5 | 1 | 17 | 1.39E−05 |
| 6 | 1 | 18 | 2.06E−05 |
| 7 | 1 | 19 | 3.71E−06 |
| 8 | 1 | 20 | 6.49E−06 |
| 9 | 1 | 21 | 3.73E−06 |

TABLE 2-continued

| | TCR variable domain (SEQ ID NO) | | |
|---|---|---|---|
| TCR No. | α | β | $K_D$ (M) |
| 10 | 1 | 22 | 1.69E−05 |
| 11 | 1 | 23 | 2.78E−05 |
| 12 | 1 | 24 | 3.93E−05 |

As can be seen from Table 2 above, the affinity of the high-affinity TCR obtained in the present disclosure for KASEKIFYV (SEQ ID NO: 29)-HLA-A0201 complex is at least twice of that of the wild-type TCR for KASEKIFYV (SEQ ID NO: 29)-HLA-A0201 complex.

Example 7 Expression, Refolding and Purification of Fusions of Anti-CD3 Antibodies with αβ Heterodimeric TCRs with High Affinity An anti-CD3 single-chain antibody (scFv) was fused with an αβ heterodimeric TCRA to prepare a fusion molecule. The anti-CD3 scFv was fused with the β chain of the TCR, where the β chain of the TCR may comprise the β chain variable domain of any one of the above αβ heterodimeric TCRs with high affinity, and the TCR α chain of the fusion molecule may comprise the α chain variable domain of any one of the above αβ heterodimeric TCRs with high affinity.

Construction of an Expression Vector for the Fusion Molecule

1. Construction of an Expression Vector for the α Chain

The target gene carrying the α chain of the αβ heterodimeric TCR was digested with NcoI and NotI and ligated with pET28a vector digested with NcoI and NotI. The ligation product was transferred into *E. coli* DH5α, plated on a kanamycin-containing LB plate, inverted and cultured at 37° C. overnight, and the positive clones were picked for PCR screening. Positive recombinants were sequenced to determine the correct sequence and the recombinant plasmid was extracted and transferred into *E. coli* Tuner (DE3) for expression.

2. Construction of an Expression Vector for Anti-CD3 (scFv)-β Chain

Primers were designed by overlap PCR to ligate the genes of the anti-CD3 scFv and the β chain of the heterodimeric TCR with high affinity. An intermediate linker was GGGGS (SEQ ID NO: 48), and the gene fragment of the fusion protein of the anti-CD3 scFv and the β chain of the heterodimeric TCR with high affinity had restriction enzyme sites NcoI (CCATGG) and NotI (GCGGCCGC). The PCR amplification product was digested with NcoI and NotI and ligated with pET28a vector digested with NcoI and NotI. The ligation product was transferred into *E. coli* DH5α competent cells, plated on a kanamycin-containing LB plate, inverted and cultured at 37° C. overnight, and the positive clones were picked for PCR screening. Positive recombinants were sequenced to determine the correct sequence and the recombinant plasmid was extracted and transferred into *E. coli* Tuner (DE3) competent cells for expression.

Expression, Refolding and Purification of Fusion Proteins

The expression plasmids were separately transferred into *E. coli* Tuner (DE3) competent cells, plated on an LB plate (kanamycin, 50 μg/mL) and cultured overnight at 37° C. On the next day, the clones were picked and inoculated into 10 mL of LB liquid medium (kanamycin, 50 μg/mL), cultured for 2-3 h, then inoculated to 1 L of LB medium at a volume ratio of 1:100, cultured until $OD_{600}$ was 0.5-0.8, and then induced to express proteins of interest using IPTG with a final concentration of 1 mM. Four hours after induction, the cells were harvested by centrifugation at 6000 rpm for 10 min. The cells were washed once in a PBS buffer and dispensed. Cells corresponding to 200 mL of the bacterial culture were taken and lysed with 5 mL of BugBuster Master Mix (Merck). The inclusion bodies were collected by centrifugation at 6000 g for 15 min. The inclusion bodies were washed 4 times with a detergent to remove cell debris and membrane components. The inclusion bodies were then washed with a buffer such as PBS to remove the detergent and salt. Finally, the inclusion bodies were dissolved in a buffer solution of 6M guanidine hydrochloride, 10 mM dithiothreitol (DTT), 10 mM ethylenediaminetetraacetic acid (EDTA), 20 mM Tris, pH 8.1, and the concentration of the inclusion bodies was determined. The inclusion bodies were dispensed and cryopreserved at −80° C.

The dissolved TCR α chain and anti-CD3 (scFv)-β chain were rapidly mixed in a mass ratio of 2:5 in 5 M urea, 0.4 M L-arginine, 20 mM Tris pH 8.1, 3.7 mM cystamine and 6.6 mM β-mercapoethylamine (4° C.), and the final concentrations of the α chain and the anti-CD3 (scFv)-β chain were 0.1 mg/mL and 0.25 mg/mL, respectively.

After mixing, the solution was dialyzed against 10 volumes of deionized water (4° C.). After 12 h, deionized water was replaced with a buffer (10 mM Tris, pH 8.0) and dialysis was continued at 4° C. for 12 h. After completion of the dialysis, the solution was filtered through a 0.45 μM filter and purified through an anion exchange column (HiTrap Q HP, 5 mL, GE Healthcare). The elution peak of the TCR containing the successfully refolded TCR α chain and anti-CD3 (scFv)-β chain dimer was confirmed by SDS-PAGE gel. The TCR fusion molecule was then purified by size-exclusion chromatography (S-100 16/60, GE Healthcare) and further purified by an anion exchange column (HiTrap Q HP, 5 mL, GE healthcare). The purity of the purified TCR fusion molecule was determined by SDS-PAGE to be greater than 90%, and the concentration thereof was determined by the BCA method.

Example 8. Activation Function Assay of Effector Cells Transfected with High-Affinity TCR of the Present Disclosure This example demonstrates that effector cells transfected with the high-affinity TCR of the present disclosure have good specific activation effects on target cells. The function and specificity of the high-affinity TCR of the present disclosure in cells were examined by ELISPOT assay.

Methods for detecting cellular function using ELISPOT assays are well known to a skilled person in the art. $CD3^+$ T cells isolated from the blood of healthy volunteers were transfected with randomly selected TCRs of the present disclosure as effector cells. The TCRs and their numbers are known from Table 2, which are respectively TCR5 (α chain variable domain SEQ ID NO: 1 and β chain variable domain SEQ ID NO: 17), TCR6 (α chain variable domain SEQ ID NO: 1 and β chain variable domain SEQ ID NO: 18), TCR7 (α chain variable domain SEQ ID NO: 1 and β chain variable domain SEQ ID NO: 19), TCR1 (α chain variable domain SEQ ID NO: 1 and β chain variable domain SEQ ID NO: 13), TCR9 (α chain variable domain SEQ ID NO: 1 and β chain variable domain SEQ ID NO: 21), TCR10 (α chain variable domain SEQ ID NO: 1 and β chain variable domain SEQ ID NO: 22), TCR2 (α chain variable domain SEQ ID NO: 1 and β chain variable domain SEQ ID NO: 14) and TCR8 (α chain variable domain SEQ ID NO: 1 and β chain variable domain SEQ ID NO: 20). Effector cells in control groups were labeled as wild-type TCR (cells transfected with a wild-type TCR) and A6 (cells transfected with another TCR). The target cell lines were K562-A2 (over-expressed A2), SW620-SSX2 (over-expressed SSX2) and K562-A11 (over-expressed A11) cells. The target cell lines K562-A2 and SW620-SSX2 were used as positive tumor cell lines; and K562-A11 was used as a negative tumor cell line as control.

Firstly, a ELISPOT plate was prepared. The ELISPOT plate was activated and coated with ethanol overnight at 4° C. On the first day of the experiment, the coating solution was removed, the plate was washed, blocked and incubated at room temperature for 2 h, and the blocking solution was removed. Components of the assay were added to the ELISPOT plate: $2\times10^4$ target cells/well and $10^3$ effector cells/well (calculated according to the positive rate of transfection) in duplicate, and incubate overnight (37° C., 5% $CO_2$). On the second day of the experiment, the plate was washed, subjected to a secondary detection and development, and dried, and the spots formed on the film were counted using an immunospot plate reader (ELISPOT READER system; AID20 company).

Experimental results are shown in FIG. 11, in which for positive target cell lines, the effector cells transfected with the high-affinity TCR of the present disclosure exhibit excellent specific activation effects and have a far better function than that of the effector cells transfected with the wild-type TCR while the effector cells transfected with another TCR have no activation effect.

All documents mentioned in the present application are hereby incorporated by reference in their entireties, as if each is incorporated by reference. In addition, it should be understood that after reading the teachings of the present disclosure described above, a skilled person in the art can make various changes or modifications of the present disclosure, and these equivalent forms also fall into the scope as defined by the appended claims of the present application.

What is claimed is:

1. A T cell receptor (TCR), wherein the TCR has an activity of binding to KASEKIFYV (SEQ ID NO: 29)-HLA A0201 complex, an α chain variable domain of the TCR comprises three CDR regions, and a β chain variable domain of the TCR comprises three CDR regions, wherein the amino acid sequences of the three CDR regions in the α chain variable domain of the TCR are listed as follows:

(SEQ ID NO: 31)
CDR1α: TSESDYY;

(SEQ ID NO: 32)
CDR2α: QEAYKQQN;

(SEQ ID NO: 30)
CDR3α: AYRSGIIQGAQKLV;

and the amino acid sequences of the three CDR regions in the β chain variable domain of the TCR are listed as follows:

(SEQ ID NO: 33)
CDR1β: PRHDT;

(SEQ ID NO: 34)
CDR2β: FYEKMQ;

(SEQ ID NO: 35)
CDR3β: ASSSDRIPPYYNEQF;

wherein the α chain variable domain of the TCR comprises an amino acid sequence having at least 90% of sequence homology with the amino acid sequence as shown in SEQ ID NO: 1; and the β chain variable domain of the TCR comprises an amino acid sequence having at least 90% of sequence homology with the amino acid sequence as shown in SEQ ID NO: 13.

2. The TCR of claim 1, wherein the affinity of the TCR for KASEKIFYV (SEQ ID NO: 29)-HLA A0201 complex is at least twice that of a wild-type TCR.

3. The TCR of claim 1, wherein the TCR is an αβ heterodimeric TCR; wherein the TCR has an α chain constant region sequence TRAC*01 and a β chain constant region sequence TRBC1*01 or TRBC2*01.

4. The TCR of claim 1, wherein the TCR is soluble.

5. The TCR of claim 1, wherein the amino acid sequence of the α chain variable domain of the TCR is SEQ ID NO: 1; and the amino acid sequence of the β chain variable domain of the TCR is SEQ ID NO: 13.

6. The TCR of claim 1, wherein an artificial interchain disulfide bond is contained between an α chain constant region and a β chain constant region of the TCR; wherein cysteine residues forming the artificial interchain disulfide bond are substituted for one or more groups of amino acids selected from the following:

Thr48 of TRAC*01 exon 1 and Ser57 of TRBC1*01 or TRBC2*01 exon 1;

Thr45 of TRAC*01 exon 1 and Ser77 of TRBC1*01 or TRBC2*01 exon 1;

Tyr10 of TRAC*01 exon 1 and Ser17 of TRBC1*01 or TRBC2*01 exon 1;

Thr45 of TRAC*01 exon 1 and Asp59 of TRBC1*01 or TRBC2*01 exon 1;

Ser15 of TRAC*01 exon 1 and Glu15 of TRBC1*01 or TRBC2*01 exon 1;

Arg53 of TRAC*01 exon 1 and Ser54 of TRBC1*01 or TRBC2*01 exon 1;

Pro89 of TRAC*01 exon 1 and Ala19 of TRBC1*01 or TRBC2*01 exon 1; and

Tyr10 of TRAC*01 exon 1 and Glu20 of TRBC1*01 or TRBC2*01 exon 1.

7. The TCR of claim 1, wherein the TCR is a single-chain TCR, wherein the single-chain TCR is formed by linking an α chain variable domain and a β chain variable domain via a flexible short peptide sequence (linker).

8. The TCR of claim 1, wherein a conjugate binds to an α chain and/or a β chain of the TCR at C- or N-terminal; wherein the conjugate is an anti-CD3 antibody.

9. A multivalent TCR complex, wherein the complex comprises at least two TCR molecules, and at least one of the TCR molecules is the TCR of claim 1.

10. An isolated cell, wherein the isolated cell expresses the TCR of claim 1; wherein the isolated cell is a T cell.

11. A pharmaceutical composition, comprising a pharmaceutically acceptable carrier, and the TCR of claim 1.

12. A method for treating a disease, comprising administering the TCR of claim 1, or an isolated cell expresses the TCR of claim 1, or a pharmaceutical composition comprising the TCR of claim 1 to a subject in need thereof.

* * * * *